(12) United States Patent
Kurn et al.

(10) Patent No.: US 7,402,386 B2
(45) Date of Patent: Jul. 22, 2008

(54) GLOBAL AMPLIFICATION USING RANDOM PRIMING BY A COMPOSITE PRIMER

(75) Inventors: Nurith Kurn, Palo Alto, CA (US); Shenglong Wang, San Mateo, CA (US)

(73) Assignee: Nugen Technologies, Inc., San Carlos, CA (US)

( * ) Notice: Subject to any disclaimer, the term of this patent is extended or adjusted under 35 U.S.C. 154(b) by 41 days.

(21) Appl. No.: 10/824,829

(22) Filed: Apr. 14, 2004

(65) Prior Publication Data

US 2005/0019793 A1 Jan. 27, 2005

Related U.S. Application Data

(60) Provisional application No. 60/462,965, filed on Apr. 14, 2003, provisional application No. 60/462,962, filed on Apr. 14, 2003.

(51) Int. Cl.
*C12Q 1/68* (2006.01)
*C12P 19/34* (2006.01)

(52) U.S. Cl. .......................................... 435/6; 435/91.1

(58) Field of Classification Search ...................... None
See application file for complete search history.

(56) References Cited

U.S. PATENT DOCUMENTS

| | | |
|---|---|---|
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 5,011,769 A | 4/1991 | Duck et al. |
| 5,043,272 A | 8/1991 | Hartley |
| 5,106,727 A | 4/1992 | Hartley et al. |
| 5,130,238 A | 7/1992 | Malek et al. |
| 5,169,766 A | 12/1992 | Schuster et al. |
| 5,185,243 A | 2/1993 | Ullman et al. |
| 5,194,370 A | 3/1993 | Berninger et al. |
| 5,270,184 A | 12/1993 | Walker |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,437,990 A | 8/1995 | Burg et al. |
| 5,455,166 A | 10/1995 | Walker |
| 5,480,784 A | 1/1996 | Kacian et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,578,832 A | 11/1996 | Trulson et al. |
| 5,589,339 A | 12/1996 | Hampson et al. |
| 5,595,891 A | 1/1997 | Rose et al. |
| 5,648,211 A | 7/1997 | Fraiser et al. |
| 5,654,142 A | 8/1997 | Kievits et al. |
| 5,660,988 A | 8/1997 | Duck et al. |
| 5,665,545 A | 9/1997 | Malek et al. |
| 5,679,512 A | 10/1997 | Laney et al. |
| 5,683,879 A | 11/1997 | Laney et al. |
| 5,700,642 A | 12/1997 | Monforte et al. |
| 5,710,028 A | 1/1998 | Eyal et al. |
| 5,712,124 A | 1/1998 | Walker |
| 5,712,127 A * | 1/1998 | Malek et al. .............. 435/91.21 |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,849 A | 6/1998 | McDonough et al. |
| 5,773,601 A | 6/1998 | Agrawal |
| 5,824,517 A * | 10/1998 | Cleuziat et al. ............ 435/91.2 |
| 5,824,518 A | 10/1998 | Kacian et al. |
| 5,830,655 A | 11/1998 | Monforte et al. |
| 5,846,710 A | 12/1998 | Bajaj |
| 5,849,547 A | 12/1998 | Cleuziat et al. |

(Continued)

FOREIGN PATENT DOCUMENTS

EP 0 050 424 4/1982

(Continued)

OTHER PUBLICATIONS

Kass et al. ("Inter-Alu polymerase chain reaction: advancements and applications" Anal Biochem. Jul. 1, 1995;228(2):185-93).*

(Continued)

*Primary Examiner*—Kenneth R. Horlick
*Assistant Examiner*—Christopher M. Babic
(74) *Attorney, Agent, or Firm*—Wilson Sonsini Goodrich & Rosati

(57) ABSTRACT

The invention relates to the field of polynucleotide amplification. More particularly, the invention provides methods, compositions and kits for amplification of (i.e., making multiple copies of) a multiplicity of different polynucleotide template sequences using a randomly primed RNA/DNA composite primer.

74 Claims, 8 Drawing Sheets

U.S. PATENT DOCUMENTS

| | | | |
|---|---|---|---|
| 5,854,033 A | 12/1998 | Lizardi | |
| 5,858,665 A | 1/1999 | Hepp et al. | |
| 5,871,697 A | 2/1999 | Rothberg et al. | |
| 5,876,976 A | 3/1999 | Richards et al. | |
| 5,882,867 A | 3/1999 | Ullman et al. | |
| 5,888,779 A | 3/1999 | Kacian et al. | |
| 5,888,819 A | 3/1999 | Goelet et al. | |
| 5,916,777 A | 6/1999 | Kacian et al. | |
| 5,932,449 A | 8/1999 | Emanuel et al. | |
| 5,932,450 A | 8/1999 | Dattagupta et al. | |
| 5,958,681 A | 9/1999 | Wetmur et al. | |
| 5,962,271 A | 10/1999 | Chenchik et al. | |
| 5,962,272 A | 10/1999 | Chenchik et al. | |
| 5,965,409 A | 10/1999 | Pardee et al. | |
| 6,004,744 A | 12/1999 | Goelet et al. | |
| 6,004,745 A | 12/1999 | Arnold, Jr. et al. | |
| 6,013,431 A | 1/2000 | Söderlund et al. | |
| 6,027,889 A | 2/2000 | Barany et al. | |
| 6,027,923 A | 2/2000 | Wallace | |
| 6,030,774 A | 2/2000 | Laney et al. | |
| 6,037,152 A | 3/2000 | Richards et al. | |
| 6,090,591 A | 7/2000 | Burg et al. | |
| 6,096,715 A | 8/2000 | Rossi et al. | |
| 6,107,032 A | 8/2000 | Kilger et al. | |
| 6,124,120 A * | 9/2000 | Lizardi | 435/91.2 |
| 6,132,997 A | 10/2000 | Shannon | |
| 6,136,533 A | 10/2000 | Bekkaoui et al. | |
| 6,143,495 A | 11/2000 | Lizardi et al. | |
| 6,159,685 A | 12/2000 | Pinkel et al. | |
| 6,218,151 B1 | 4/2001 | Cleuziat et al. | |
| 6,251,600 B1 | 6/2001 | Winger et al. | |
| 6,251,639 B1 * | 6/2001 | Kurn | 435/91.2 |
| 6,270,961 B1 | 8/2001 | Drmanac | |
| 6,280,949 B1 | 8/2001 | Lizardi | |
| 6,291,170 B1 | 9/2001 | Van Gelder et al. | |
| 6,358,712 B1 | 3/2002 | Jarrell et al. | |
| 6,365,375 B1 | 4/2002 | Dietmaier et al. | |
| 6,410,278 B1 | 6/2002 | Notomi et al. | |
| 6,686,156 B2 | 2/2004 | Kurn | |
| 6,692,918 B2 * | 2/2004 | Kurn | 435/6 |
| 6,946,251 B2 * | 9/2005 | Kurn | 435/6 |
| 2001/0000077 A1 | 3/2001 | Engelhardt et al. | |
| 2001/0034048 A1 | 10/2001 | Kurn | |
| 2001/0041334 A1 | 11/2001 | Rashtchian et al. | |
| 2002/0115088 A1 | 8/2002 | Kurn | |
| 2002/0127575 A1 | 9/2002 | Hoke et al. | |
| 2002/0142309 A1 | 10/2002 | Dattagupta | |
| 2002/0164628 A1 | 11/2002 | Kurn | |
| 2002/0177141 A1 | 11/2002 | Chee et al. | |
| 2003/0073081 A1 | 4/2003 | Mukai et al. | |
| 2003/0087251 A1 | 5/2003 | Kurn | |
| 2003/0104460 A1 | 6/2003 | Rabbani et al. | |
| 2003/0186234 A1 | 10/2003 | Kurn | |
| 2003/0215926 A1 | 11/2003 | Kurn et al. | |
| 2004/0005614 A1 | 1/2004 | Kurn et al. | |
| 2004/0023271 A1 | 2/2004 | Kurn et al. | |

FOREIGN PATENT DOCUMENTS

| | | |
|---|---|---|
| EP | 0 084 796 | 8/1983 |
| EP | 0 201 184 | 12/1986 |
| EP | 0 237 362 | 9/1987 |
| EP | 0 258 017 | 3/1988 |
| EP | 0 320 308 | 6/1989 |
| EP | 0 365 627 | 5/1990 |
| EP | 0 395 398 | 10/1990 |
| EP | 0 497 272 | 8/1992 |
| EP | 0 500 224 | 8/1992 |
| EP | 0 505 012 | 9/1992 |
| EP | 0 543 612 | 5/1993 |
| EP | 0 667 393 | 8/1995 |
| EP | 0 878 553 | 11/1998 |
| EP | 0 971 039 | 1/2000 |
| EP | 1 055 736 | 11/2000 |
| EP | 1 167 524 | 1/2002 |
| EP | 1 275 737 | 1/2003 |
| EP | 1 281 757 | 2/2003 |
| EP | 1 312 682 | 5/2003 |
| JP | 06-327500 | 11/1994 |
| JP | 07-023799 | 1/1995 |
| WO | WO 88/02746 | 4/1988 |
| WO | WO 88/10315 | 12/1988 |
| WO | WO 89/01050 | 2/1989 |
| WO | WO 92/15712 | 9/1992 |
| WO | WO 95/03426 | 2/1995 |
| WO | WO 97/04126 | 2/1997 |
| WO | WO 97/32040 | 9/1997 |
| WO | WO 98/28443 | 7/1998 |
| WO | WO 99/18241 | 4/1999 |
| WO | WO 99/23256 | 5/1999 |
| WO | WO 99/29901 | 6/1999 |
| WO | WO 99/37808 | 7/1999 |
| WO | WO 99/40219 | 8/1999 |
| WO | WO 99/42618 | 8/1999 |
| WO | WO 99/55912 | 11/1999 |
| WO | WO 00/08208 | 2/2000 |
| WO | WO 00/09745 | 2/2000 |
| WO | WO 00/28082 | 5/2000 |
| WO | WO 00/40715 | 7/2000 |
| WO | WO 00/52191 | 9/2000 |
| WO | WO 00/56877 | 9/2000 |
| WO | WO 00/56925 | 9/2000 |
| WO | WO 00/70095 | 11/2000 |
| WO | WO 01/20035 | 3/2001 |
| WO | WO 01/23613 | 4/2001 |
| WO | WO 01/64952 | 9/2001 |
| WO | WO 01/73134 | 10/2001 |
| WO | WO 02/00938 | 1/2002 |
| WO | WO 02/28876 | 4/2002 |
| WO | WO 02/29117 | 4/2002 |
| WO | WO 02/48402 | 6/2002 |
| WO | WO 02/057487 | 7/2002 |
| WO | WO 02/072772 | 9/2002 |
| WO | WO 02/072773 | 9/2002 |
| WO | WO 02/103013 | 12/2002 |
| WO | WO 03/012100 | 2/2003 |
| WO | WO 03/012142 | 2/2003 |
| WO | WO 03/078645 | 9/2003 |
| WO | WO 03/083435 | 10/2003 |

OTHER PUBLICATIONS

U.S. Appl. No. 10/686,466, filed Oct. 14, 2003, Kurn.
U.S. Appl. No. 10/713,696, filed Nov. 14, 2003, Kurn.
U.S. Appl. No. 10/857,160, filed May 28, 2004, Kurn.
U.S. Appl. No. 10/913,246, filed Aug. 5, 2004, Kurn.
Ausubel, F.M. et al. eds. (1995). *Current Protocols in Molecular Biology.* Johm Wiley & Sons, Inc. pp. iii-xii (Table of Contents Only.).
Blanchard, A.P. et al. (1996). "High-Density Oligonucleotide Arrays," *Biosensors & Bioelectronics*, 11(6/7):687-690.
Caruthers, M.H. et al. (1987). "Chemical Synthesis of Deoxyoligonucleotides by the Phosphoramidite Method" Chapter 15 *In Methods In Enzymology* 154:287-313.
Daigo, Y. et al. (May 2001). "Degenerate Oligonucleotide Primed-Polymerase Chain Reaction-Based Array Comparative Genomic Hybridization for Extensive Amplicon Profiling of Breast Cancers," *Am. J. Pathol.* 158(5):1623-1631.
Dean, F.B. et al. (Apr. 16, 2002). "Comprehensive Human Genome Amplification Using Multiple Displacement Amplification," *Proc. Natl. Acad. Sci. USA* 99(8):5261-5266.
DeRisi, J. et al. (Dec. 1996). "Use of cDNA Microarray to Analyse Gene Expression Patterns in Human Cancer," *Nature Genetics* 14:457-460.

Dietmaier, W. et al. (Jan. 1999). "Multiple Mutation Analyses in Single Tumor Cells with Improved Whole Genome Amplification," *Am. J. Pathol.* 154(1):83-95.

Flanagan, W. M. et al. (Mar. 1999). "A Cytosine Analog That Confers Enhanced Potency to Antisense Oligonucleotides," *Proc. Natl. Acad. Sci. USA* 96(7):3513-3518.

Fodor, S.P.A. et al. (Feb. 1991) "Light-Directed, Spatially Addressable Parallel Chemical Synthesis," *Science* 251:767-773.

Freier, S.M. et al. (Dec. 1986). "Improved Free-Energy Paramenters for Predictions of RNA Duplex Stability," *Proc. Natl. Acad. Sci. USA* 83:9373-9377.

Freshney, R.I. ed. (1987). *Animal Cell Culture.* IRL Press: Oxford, pp. vii-xii (Table of Contents Only.).

Fu, D-J. et al. (1997). "Sequencing Double-Stranded DNA by Strand Displacement," *Nucleic Acids Research* 25(3):677-679.

Gait, M.J. ed. (1984). *Oligonucleotide Synthesis: A Practical Approach.* IRL Press: Oxford, pp. vii-xii (Table of Contents Only.).

Gasparini, P. et al. (1996). "Scanning the First Part of the Neurofibromatosis Type 1 Gene by RNA-SSCP: Identification of Three Novel Mutations and of Two New Polymorphisms," *Hum. Genet.* 97:492-495.

Guatelli, J.C. et al. (Mar. 1990). "Isothermal, in vitro Amplification of Nucleic Acids by a Multienzyme Reaction Modeled After Retroviral Replication," *Proc. Natl. Acad. Sci. USA* 87:1874-1878.

Gubler, U. et al. (1983). "A Simple and Very Efficient Method for Generating cDNA Libraries," *Gene* 25:263-269.

International Search Report mailed on Oct. 15, 2004 for PCT Application No. PCT/US2004/012779 filed on Apr. 14, 2004, 8 pages.

Khrapko, K.R. et al. (1991). "A Method for DNA Sequencing by Hybridization with Oligonucleotide Matrix," *DNA Sequence—J. DNA Sequencing and Mapping* 1:375-388.

Kumar, R. et al. (1998). "The First Analogues of LNA (Locked Nucleic Acids): Phosphorothioate-LNA and 2'-Thio-LNA," *Bioorg. Med. Chem. Lett.* 8:2219-2222.

Kwoh, D.Y. et al. (Feb. 1989). "Transcription-Based Amplification System and Detection of Amplified Human Immunodeficiency Virus Type 1 with a Bead-Based Sandwich Hybridization Format," *Proc. Natl. Acad. Sci. USA* 86:1173-1177.

Lishanski, A. et al. (2000). "Branch Migration Inhibition in PCR-Amplified DNA: Homogeneous Mutation Detection," *Nucl. Acids Res.* 28(9):E42, pp. i-vii.

Lockhart, D.J. et al. (Dec. 1996). "Expression Monitoring by Hybridization to High-Density Oligonucleotide Arrays," *Nature Biotechnology* 14:1675-1680.

Marshall, A. et al. (Jan. 1998). "DNA Chips: An Array of Possibilities," *Nature Biotechnol.* 16:27-31.

Maskos, U. et al. (1992). "Oligonucleotide Hybridisations on Glass Supports: a Novel Linker for Oligonucleotide Synthesis and Hybridisation Properties of Oligonucleotides Synthesised in situ," *Nucl. Acids. Res.* 20(7):1679-1684.

Matson, R.S. et al. (1995). "Biopolymer Synthesis on Polypropylene Supports: Oligonucleotide Arrays," *Anal Biochem.* 224(1):110-116.

Mullis, K. et al. (1986). "Specific Enzymatic Amplification of DNA In Vitro: the Polymerase Chain Reaction," *Cold Spring Harbor Symp. Quant. Biol.* 51:263-273.

Mullis, K.B et al. eds. (1994). *PCR: The Polymerase Chain Reaction.* Birkhäuser: Boston, pp. xv-xvii (Table of Contents Only.).

Okayama, H. et al. (Feb. 1982). "High Efficiency Cloning of Full-Length cDNA" *Molecular and Cell Biology* 2(2):161-170.

Orita, M. et al. (Apr. 1989). "Detection of Polymorphisms of Human DNA by Gel Electrophoresis as Single-Strand Conformation Polymorphisms," *Proc. Natl. Acad. Sci. USA* 86(8):2766-2770.

Orita, M. et al. (1989). "Rapid and Sensitive Detection of Point Mutations and DNA Polymorphisms Using the Polymerase Chain Reaction," *Genomics* 5(4):874-879.

Patel, R. et al. (Apr. 1996). "Formation of Chimeric DNA Primer Extension Products by Template Switching Onto an Annealed Downstream Oligonucleotide," *Proc. Natl. Acad. Sci. USA* 93:2969-2974.

Pease, A.C. et al. (May 1994). "Light-Generated Oligonucleotide Arrays for Rapid DNA Sequence Analysis," *Proc. Natl. Acad. Sci. USA* 91:5022-5026.

Ramsay, G. (Jan. 1998). "DNA chips: State-of-the art," *Nature Biotechnol.* 16(1):40-44.

Saiki, R.K. et al. (Jan. 29, 1988). "Primer-Directed Enzymatic Amplification of DNA with a Thermostable DNA Polymerase," *Science* 239:487-491.

Sambrook, J. et al., eds. (1989). *Molecular Cloning: A Laboratory Manual.* 2nd Edition, Cold Spring Harbor Laboratory Press, pp. xi-xxxviii (Table of Contents Only.).

Sarkar, G. et al. (1992). "Screening for Mutations by RNA Single-Strand Conformation Polymorphism (rSSCP): Comparison with DNA-SSCP," *Nucl. Acids Res.* 20(4):871-878.

Sasaki, N. et al. (Mar. 1998). "Transcriptional Sequencing: A Method for DNA Sequencing Using RNA Polymerase," *Proc. Natl. Acad. Sci. USA* 95:3455-3460.

Scaringe, S.A. et al. (1998). "Novel RNA Synthesis Method Using 5'-O-Silyl-2'-O-orthoester Protecting Groups," *J. Am. Chem. Soc.* 120:11820-11821.

Scaringe, S.A. (2000). "Advanced 5'-Silyl-2'-Orthoester Approach to RNA Oligonucleotide Synthesis," Chapter 1 *In Methods In Enzymology* 317:3-18.

Schena, M. et al. (Oct. 20, 1995). "Quantitative Monitoring of Gene Expression Patterns with a Complementary DNA Microarray," *Science* 270:467-470.

Schena, M. et al. (Oct. 1996). "Parallel Human Genome Analysis: Microarray-Based Expression Monitoring of 1000 Genes," *Proc. Natl. Acad. Sci. USA* 93:10614-10619.

Shalon, D. et al. (1996) "A DNA Microarray System for Analyzing Complex DNA Samples Using Two-Color Fluorescent Probe Hybridization," *Genome Res.* 6:639-645.

Stoecklein, N.H. et al. (Jul. 2002). "SCOMP Is Superior to Degenerated Oligonucleotide Primed-Polymerase Chain Reaction for Global Amplification of Minute Amounts of DNA From Microdissected Archival Tissue Samples," *Am. J. Pathol.* 161(1):43-51.

Suzuki, Y. et al. (1990). "Detection of *ras* Gene Mutations in Human Lung Cancers by Single-Strand Conformation Polymorphism Analysis of Polymerase Chain Reaction Products," *Oncogene* 5:1037-1043.

Tinoco, I. Jr. et al. (1973). "Improved Estimation of Secondary Structure in Ribonucleic Acids," *Nature* 246:40-41.

Wahlestedt, C. et al. (May 9, 2000). "Potent and Nontoxic Antisense Oligonucleotides Containing Locked Nucleic Acids," *Proc. Natl. Acad. Sci. USA* 97(10):5633-5638.

Walker, G.T. et al. (Jan. 1992). "Isothermal in vitro Amplification of DNA by a Restriction Enzyme/DNA Polymerase System," *Proc. Natl. Acad. Sci. USA* 89:392-396.

Wang, V.W. et al. (May 15, 2001). "Whole Genome Amplification and High-Throughput Allelotyping Identified Five Distinct Deletion Regions on Chromosomes 5 and 6 in Microdissected Early-Stage Ovarian Tumors," *Can Res.* 61:4169-4174.

Wang, E. et al. (Apr. 2000). "High Fidelity mRNA Amplification for Gene Profiling," *Nature Biotechnology* 18:457-459.

Wiltshire, S. et al. (2000). "Detection of Multiple Allergen-Specific IgEs on Microarrays by Immunoassay with Rolling Circle Amplification," *Clinical Chem.* 46(12):1990-1993.

Wu, D.Y. et al. (1989). "The Ligation Amplification Reaction (LAR)—Amplification of Specific DNA Sequences Using Sequential Rounds of Template-Dependent Ligation," *Genomics* 4:560-569.

Zheng, S. et al. (Jun. 2001). "Whole Genome Amplification Increases the Efficiency and Validity of Buccal Cell Genotyping in Pediatric Populations," *Cancer Epidemiol.* 10:697-700.

Kricka. Nonisotopic DNA Probe Techniques. Academic Press 1992.

Tijessen. Hybridization with Nucleic Acid Probes. Elsevier Science Publishers. 1993.

Wang, et al. Whole genome amplification and high-throughput allelotyping identified five distinct deletion regions on chromosomes 5 and 6 in microdissected early-stage ovarian tumors. Cancer Res. 2001; 61:4169-4174.

Kurn, et al. U.S. Appl. No. 60/533,381, entitled "Methods for fragmentation, labeling and immobilization of nucleic acids," filed Dec. 29, 2003.

Kurn, et al. U.S. Appl. No. 60/381,457, entitled "Methods for fragmentation, labeling and immobilization of nucleic acids," filed May 17, 2002.

\* cited by examiner

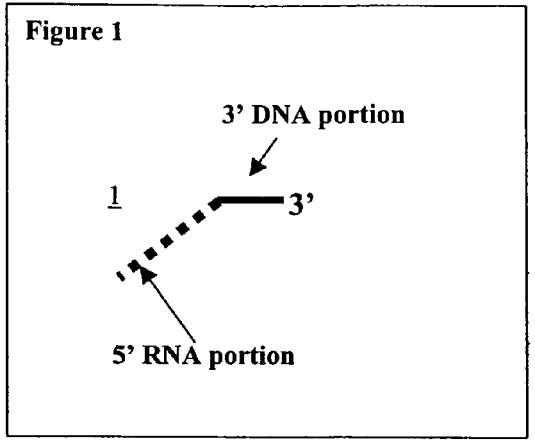
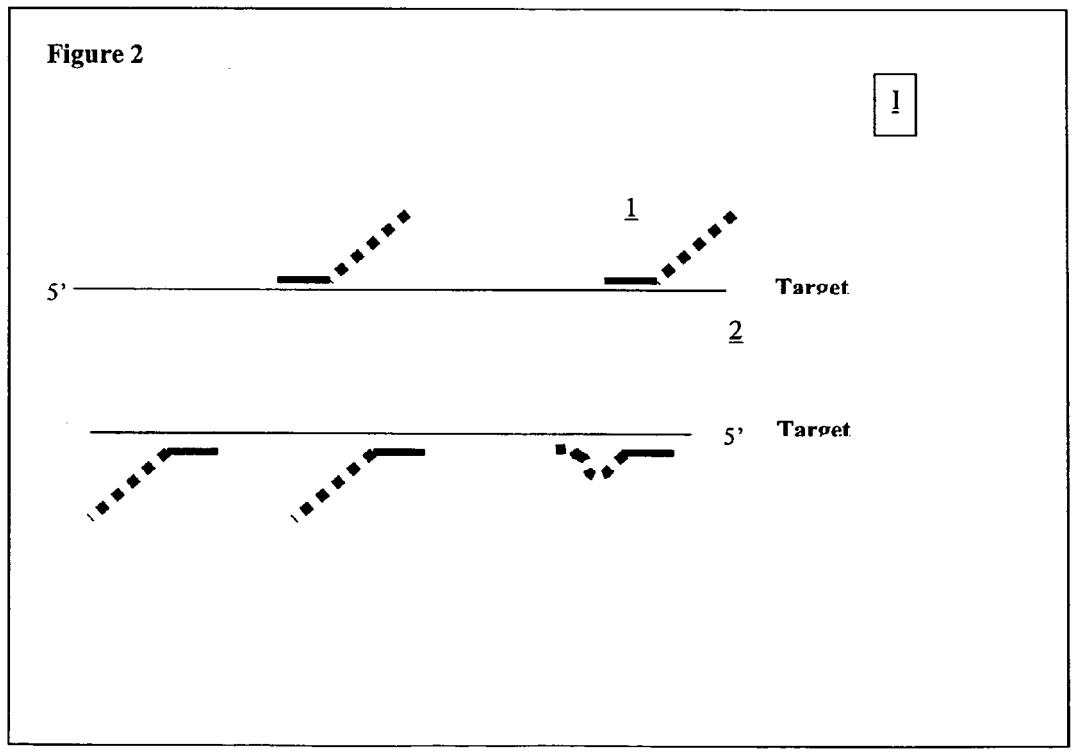

Figure 7A
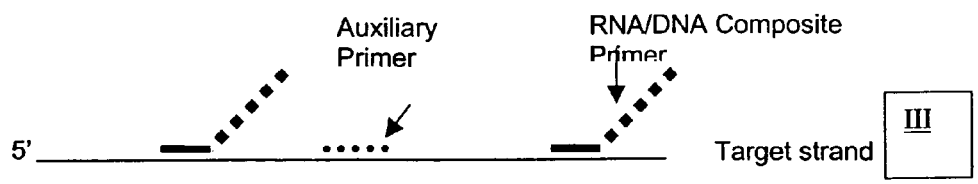
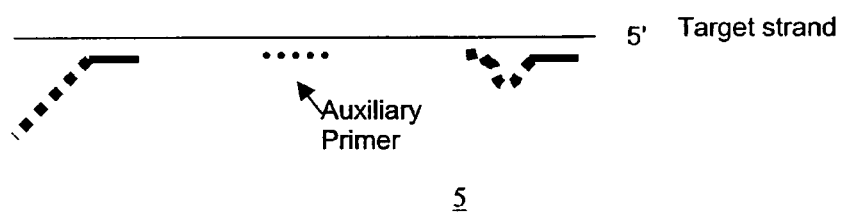
Figure 7B
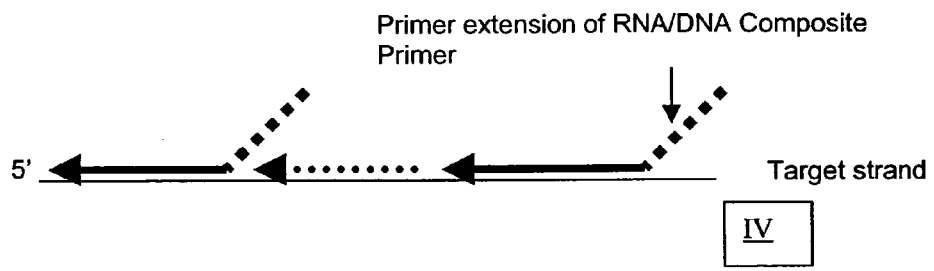
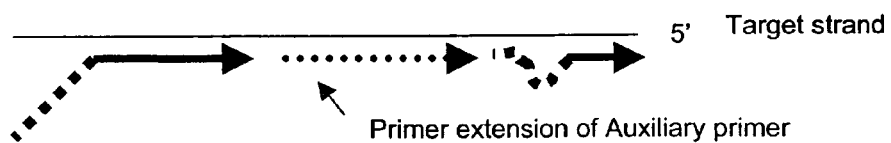

GLOBAL AMPLIFICATION USING RANDOM PRIMING BY A COMPOSITE PRIMER

CROSS-REFERENCE TO RELATED APPLICATIONS

This application claims priority under 35 U.S.C. § 119(e) to U.S. Provisional Patent Applications Nos. 60/462,962, filed Apr. 14, 2003, and 60/462,965, filed Apr. 14, 2003, each of which is incorporated by reference in its entirety.

TECHNICAL FIELD

The invention relates to the field of polynucleotide amplification. More particularly, the invention provides methods, compositions and kits for amplifying (i.e., making multiple copies of) a multiplicity of different polynucleotide template sequences using a randomly primed RNA/DNA composite primer.

BACKGROUND ART

The quality and quantity of nucleic acid (e.g. genomic DNA) sample is important for many studies. High-throughput genomic analysis requires large amounts of template for testing, yet typically the yield of nucleic acids from individual patient samples is limited. Forensic and paleoarcheology work also can be severely limited by nucleic acid sample size. The limitation of starting material impacts the ability to carry out large scale analysis of multiple parameters, as is required for, for example, the genotyping of multiple loci in the study of complex diseases. Moreover, it is well accepted that molecular analysis determination of genomic instability in various pathological condition such as cancer, is most precisely carried out in well defined cell populations, such as that obtained by laser capture micro-dissection or cell sorting. Nucleic acid amplification technologies that provide global amplification of very small polynucleotide samples, for example, from one or a very few cells, may provide a solution to the limited starting materials generally available for analysis.

Likewise, the ability to amplify ribonucleic acid (RNA) is an important aspect of efforts to elucidate biological processes. Total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like. Non-coding RNAs have been shown to be of great importance in regulation of various cellular functions and in certain disease pathologies. Such RNAs are often present in very low levels. Thus, amplification methods capable of amplifying low abundance RNAs, including RNAs that are not polyadenylated, are of great importance.

Various methods for global amplification of DNA target molecules (e.g., whole genome amplification) have been described, including methods based on the polymerase chain reaction (PCR). See, e.g., U.S. Pat. Nos. 5,731,171; 6,365,375; Daigo et al., (2001) Am. J. Pathol. 158 (5):1623-1631; Wang et al, (2001); Cancer Res. 61:4169-4174; Zheng et al, (2001) Cancer Epidemiol. 10:697-700; Dietmaier et al (1999) Am. J. Pathol. 154 (1) 83-95; Stoecklein et al (2002) Am. J. Pathol. 161 (1):43-51; U.S. Pat. Nos. 6,124,120; 6,280,949; Dean et al (2002) PNAS 99 (8):5261-5266. However, PCR-based global amplification methods, such as whole genome amplification (WGA), may generate non-specific amplification artifacts, give incomplete coverage of loci, or generate DNA of insufficient length that cannot be used in many applications. PCR-based methods also suffer from the propensity of the PCR reaction to generate products that are preferentially amplified, and thus resulting in biased representation of genomic sequences in the products of the amplification reaction.

Additionally, a number of methods for the analysis of gene expression have been developed in recent years. See, for example, U.S. Pat. Nos. 6,251,639, 6,692,918, 6,686,156, 5,744,308; 6,143,495; 5,824,517; 5,829,547; 5,888,779; 5,545,522; 5,716,785; 5,409,818; EP 0971039A2; EP0878553A2; and U.S. published patent applications nos. 2002/0115088, 2003/0186234, 2003/0087251, and 2004/0023271. These include quantification of specific mRNAs, and the simultaneous quantification of a large number of mRNAs, as well as the detection and quantification of patterns of expression of known and unknown genes. RNA amplification is most commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by polymerase chain reaction (PCR) amplification to produce multiple copies of double stranded DNA. Although these methods are most commonly used, they have some significant drawbacks: a) the reactions require thermocycling; b) the products are double stranded, thus rendering them less accessible to binding to probes; and c) the reactions are prone to contamination with products of prior amplification, thus requiring strict containment of reaction mixtures. Other current RNA amplification methods use initiation of replication of mRNA from the poly-A tail at their 3' ends. However, not all RNA transcripts have a mRNA tail (for example, prokaryotic RNAs and non-coding RNAs). In addition, due to sample preparation procedures, the RNA transcript structural integrity is compromised. Thus, it may be desirable in certain circumstances to use RNA amplification methods that do not require initiation of replication at the defined poly-A tail. Although analysis of non-amplified RNA is feasible, a significant amount of starting RNA would be required. However, the total amount of sample RNA that is available is frequently limited by the amount of biological sample from which it is derived. Biological samples are often limited in amount and precious. Moreover, the amount of the various RNA species is not equal; some species are more abundant than others are, and these are more likely and easier, to analyze. The ability to amplify RNA sequences enables the analysis of less abundant, rare RNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components.

Therefore, there is a need for improved amplification methods, particularly methods which can globally amplify DNA or RNA polynucleotide targets. The invention described herein fulfills this need.

All references cited herein, including patent applications and publications, are incorporated by reference in their entirety.

DISCLOSURE OF THE INVENTION

The invention provides methods, compositions, and kits for isothermal global amplification using a randomly hybridized RNA/DNA composite primer, as well as applications of the amplification methods.

Accordingly, in one aspect, the invention provides methods for amplification of a template polynucleotide, said methods comprising: (a) incubating a reaction mixture, said reaction mixture comprising: (i) a template polynucleotide; (ii) a first primer, wherein the first primer is a composite primer that is hybridizable to a multiplicity of template polynucleotide sites, wherein the composite primer comprises an RNA portion and a 3' DNA portion; (iii) a DNA-dependent DNA polymerase; and (iv) an RNA-dependent DNA polymerase (which may be present as a separate enzyme or as an enzyme comprising both DNA-dependent DNA polymerase and RNA-dependent DNA polymerase activities); wherein the incubation is under conditions that permit composite primer random hybridization, primer extension and, in some embodiments, displacement of the primer extension product from template polynucleotide, whereby a complex comprising an RNA/DNA partial heteroduplex is generated; and (b) incubating a reaction mixture, said reaction mixture comprising (i) the reaction products generated according to step (a) (or an aliquot thereof); (ii) a composite primer (which may be the same as the first primer, or may be a different primer), wherein the composite primer comprises an RNA portion and a 3' DNA portion; (iii) an DNA-dependent DNA polymerase; and (iv) an agent (such as an enzyme) that cleaves RNA from an RNA/DNA hybrid; wherein the incubation is under conditions that permit RNA cleavage from an RNA/DNA heteroduplex, primer hybridization, primer extension, and displacement of the primer extension product from the complex of (a) when its RNA is cleaved and another composite primer binds to the template and is extended, whereby multiple copies of a polynucleotide (generally, DNA) amplification product are generated. In embodiments wherein the template polynucleotide is RNA, the reaction mixture of step (a) further comprises (v) an agent (such as an enzyme)that cleaves RNA from an RNA/DNA hybrid, whereby template RNA is cleaved form the complex comprising template RNA and first primer extension product. In some embodiments, the reaction mixture of step (b) comprises the reaction mixture according to step (a) (or an aliquot thereof). In other embodiments, step (b) is initiated by the addition of an agent that cleaves RNA from a partial RNA/DNA heteroduplex (such as RNase H), and optionally, a DNA-dependent DNA polymerase, to the reaction mixture of step (a). In some embodiments, the reaction mixture of step (a) and/or (b) further comprises auxiliary primers. In some embodiments (generally embodiments in which the template polynucleotide is DNA), the RNA-dependent DNA polymerase may be omitted from reaction mixture (a).

In another aspect, the invention provides methods for amplification of a template polynucleotide by incubating a reaction mixture, said reaction mixture comprising: (a) a complex comprising a RNA/DNA partial heteroduplex, wherein the complex is generated by incubating a first reaction mixture, said first reaction mixture comprising: (i) a polynucleotide template; (ii) a first primer; wherein the first primer is a composite primer, the composite primer comprising a RNA portion and a 3' DNA portion; and wherein the composite primer is capable of hybridizing to a multiplicity of template polynucleotide sites; (iii) a DNA-dependent DNA polymerase; and (iv) an RNA-dependent DNA polymerase; wherein the incubation is under conditions that permit composite primer random hybridization, primer extension and displacement of the primer extension product from template polynucleotide, whereby a complex comprising an RNA/DNA partial heteroduplex is generated; (b) a composite primer, wherein the composite primer comprises an RNA portion and a 3' DNA portion; (c) a DNA-dependent DNA polymerase; and (d) an enzyme that cleaves RNA from an RNA/DNA hybrid; wherein the incubation is under conditions that permit primer hybridization, primer extension, RNA cleavage from an RNA/DNA heteroduplex, and displacement of composite primer from the complex of step (a) when its RNA is cleaved and another composite primer binds and is extended, whereby multiple copies of a polynucleotide amplification product are generated. In some embodiments, the reaction mixture and/or first reaction mixture further comprises auxiliary primers. In some embodiments wherein the template polynucleotide is RNA, template RNA in step (a) is cleaved following primer extension via conditions or agents promoting cleavage. In some embodiments, the first reaction mixture further comprises: (v) an agent (such as an enzyme) that cleaves RNA from an RNA/DNA hybrid, whereby template RNA is cleaved from the complex comprising template RNA and composite primer extension product. In some embodiments (generally those in which the template polynucleotide is DNA), the complex comprising a RNA/DNA partial heteroduplex may be generated without the use of RNA-dependent DNA polymerase.

In another aspect, the invention provides methods for amplification of a template polynucleotide by incubating a reaction mixture, said reaction mixture comprising: (a) a complex of a first primer extension product and a second primer extension product, wherein the first primer extension product is generated by extension of a randomly primed first primer hybridized to target polynucleotide with a DNA polymerase, wherein the first primer is a composite primer comprising an RNA portion and a 3' DNA portion, wherein the first primer is capable of hybridizing to a multiplicity of template polynucleotide sites, and wherein the second primer extension product is generated by extension of a second primer hybridized to the first primer extension product; (b) a composite primer that is hybridizable to the second primer extension product, wherein the composite primer comprises an RNA portion and a 3' DNA portion; (c) a DNA-dependent DNA polymerase; and (d) an enzyme that cleaves RNA from an RNA/DNA hybrid; wherein the incubation is under conditions that permit primer hybridization, primer extension, RNA cleavage from an RNA/DNA heteroduplex, and displacement of composite primer from the complex of step (a) when its RNA is cleaved and another composite primer binds and is extended, whereby multiple copies of a polynucleotide amplification product are generated. In some embodiments wherein the template polynucleotide is RNA, the first primer extension product is generated by extension of a randomly primed first primer hybridized to target RNA with a RNA-dependent DNA polymerase. In some embodiments, the first primer extension product and/or the second primer extension product are generated in the presence of auxiliary primers.

In another aspect, the invention provides methods for amplification of a polynucleotide template comprising: (a) random priming of polynucleotide template strand with a composite primer; wherein the composite primer comprises an RNA portion and a 3' DNA portion, and wherein the composite primer is capable of hybridizing to a multiplicity of template polynucleotide sites; and (b) incubating template strand in the presence of a DNA-dependent DNA polymerase, an RNA-dependent DNA polymerase, and an agent that cleaves RNA from an RNA/DNA, whereby multiple copies of polynucleotide amplification product are generated via primer extension and strand displacement. In some embodiments, random priming occurs in the presence of a DNA polymerase. In some embodiments, auxiliary primers are included in step (a) and/or step (b). In some embodiments (generally those in which the polynucleotide template is DNA), the RNA-dependent DNA polymerase is omitted from the incubation.

In another aspect, the invention provides methods for amplification of RNA template polynucleotides which operate as follows: a multiplicity of template polynucleotide sequences are amplified by incubating a reaction mixture, the reaction mixture comprising: (a) a complex of a first primer extension product and a second primer extension product, wherein the first primer extension product is generated by extension of a first primer hybridized to template RNA strand with an RNA-dependent DNA polymerase, wherein the first primer is a composite primer comprising an RNA portion and a 3' DNA portion, wherein the first primer is capable of hybridizing to a multiplicity of sites on template RNA; wherein the second primer extension product is generated by extension of a second primer hybridized to the first primer extension product; and wherein RNA from the complex of first and second primer extension product is cleaved (using e.g., an enzyme that cleaves RNA from an RNA/DNA hybrid or conditions permitting cleavage, such as heat and/or alkaline conditions); (b) a composite primer that is hybridizable to the second primer extension product, wherein the composite primer comprises an RNA portion and a 3' DNA portion; (c) a DNA-dependent DNA polymerase; and (d) an enzyme that cleaves RNA from an RNA/DNA hybrid; wherein the incubation is under conditions that permit primer hybridization, primer extension, RNA cleavage from an RNA/DNA heteroduplex, and displacement of composite primer from the complex of step (a) when its RNA is cleaved and another composite primer binds to the second primer extension product and is extended, whereby multiple copies of polynucleotide amplification product are generated. In some embodiments, the complex of step (a) is generated in the presence of auxiliary primers. In some embodiments, the second primer comprises fragment(s) of cleaved RNA template.

In another aspect, the invention provides methods for amplification of a template polynucleotide by (a) randomly priming a template polynucleotide with a first primer, wherein said first primer is a composite primer that is hybridizable to a multiplicity of template polynucleotide sites, wherein the composite primer comprises a RNA portion and a 3' DNA portion; (b) extending the first primer with a DNA polymerase; (c) cleaving RNA from the first primer with an agent that cleaves RNA from a RNA/DNA heteroduplex; (d) hybridizing an amplification primer to the template polynucleotide, wherein said amplification primer is a composite primer comprising a RNA portion and a 3' DNA portion; (e) extending the hybridized amplification primer by strand displacement DNA synthesis; and (f) cleaving RNA from the amplification primer with an agent that cleaves RNA from a RNA/DNA heteroduplex, such that another amplification primer can hybridize and be extended, whereby multiple copies of a polynucleotide amplification product are generated.

In another aspect, the invention provides methods for amplification of a template polynucleotide by incubating a reaction mixture including: (a) a polynucleotide template strand; (b) a first primer, wherein said first primer is a composite primer comprising a RNA portion and a 3' DNA portion, and wherein the first primer is capable of hybridizing to a multiplicity of template polynucleotide sites; (c) a DNA-dependent DNA polymerase; (d) a RNA-dependent DNA polymerase; and (e) an agent that cleaves RNA from a RNA/DNA heteroduplex, whereby multiple copies of polynucleotide amplification product are generated by primer extension and strand displacement. In some embodiments (generally those embodiments in which the polynucleotide template is DNA), the RNA-dependent DNA polymerase is omitted from the reaction mixture.

As is clear to one skilled in the art, reference to production of copies of a polynucleotide (e.g., DNA or RNA) template or copies of a polynucleotide sequence complementary to a polynucleotide template refers to products that may contain, comprise or consist of such sequences. As is evident to one skilled in the art, aspects that refer to combining and incubating the resultant mixture also encompasses method embodiments which comprise incubating the various mixtures (in various combinations and/or subcombinations) so that the desired products are formed.

Various embodiments of the composite primer(s) used in the methods of the invention are described herein. For example, in some embodiments, the RNA portion of a composite primer is 5' with respect to the 3' DNA portion. In still other embodiments, the 5' RNA portion is adjacent to the 3' DNA portion. In other embodiments, the RNA portion of the composite primer consists of 7 to about 20 nucleotides and the DNA portion of the composite primer consists of about 5 to about 20 nucleotides. In still other embodiments, the RNA portion of the composite primer consists of about 10 to about 20 nucleotides and the DNA portion of the composite primer consists of about 7 to about 20 nucleotides. In some embodiments the composite primer is selected from the following composite primers: 5'-GACGGAUGCGGUCUdCdCdAdGdTdGdT-3 (SEQ ID NO:1); and 5'-CGUAUUCUGACGACGUACUCdTdCdAdGdCdCdT-3' (SEQ ID NO:2), wherein italics denote ribonucleotides and "d" denotes deoxyribonucleotides.

In some embodiments, the composite primer comprises random sequence or partially randomized sequence, although certain embodiments (such as certain embodiments wherein the template polynucleotide is RNA) exclude the use of primers comprising random or partially random sequence. In embodiments utilizing a composite primer with random or partially random sequence, the composite primer may be a population or pool of different primers comprising at least 2, at least 3, at least 4, at least 5, at least 10, at least 15, at least 20, at least 30, at least 40, at least 50, or at least 100 different sequences. In other embodiments, the composite primer contains one or more "degenerate" nucleotides that is able to hybridize to multiple different nucleotide bases (e.g., inosine, which is able to hybridize to all four canonical bases).

In some embodiments, the composite primer that hybridizes to target polynucleotide (such as mRNA or genomic DNA) and the composite primer used during single primer isothermal amplification (i.e., phase (b) of the methods) are the same. In some embodiments, the composite primer that hybridizes to target polynucleotide (such as mRNA or genomic DNA) and the composite primer used during single primer isothermal amplification are different. In some embodiments, two (or more) different composite primers that hybridize to target polynucleotide are used in the methods of the invention.

The methods are applicable to amplifying any target polynucleotide, including, for example, DNA (such as genomic DNA, including human and other mammalian genomic DNA) and RNA (such as total RNA, mRNA, noncoding RNA and ribosomal RNA). One or more steps may be combined and/or performed sequentially (often in any order, as long as the requisite product(s) are able to be formed), and, as is evident, the invention includes various combinations of the steps described herein. It is also evident, and is described herein, that the invention encompasses methods in which the initial, or first, step is any of the steps described herein. For example, the methods of the invention do not require that the first step be random hybridization of composite primer. Methods of the invention encompass embodiments in which later, "downstream" steps are an initial step.

The enzymes which may be used in the methods and compositions are described herein. For example, the agent (such as an enzyme) that cleaves RNA may be an RNase H, and the RNA-dependent DNA polymerase may be reverse transcriptase. The RNA-dependent DNA polymerase may comprise an RNase H enzyme activity, or separate enzymes may be used. Similarly, a DNA polymerase may comprise both RNA-dependent and DNA-dependent DNA polymerase enzyme activities, or separate enzymes may be used. A DNA-dependent DNA polymerase, an RNA-dependent DNA polymerase, and the enzyme that cleaves RNA can also be the same enzyme, or separate enzymes comprising each of these activities may be used.

In some embodiments, methods of the invention are used to generate labeled polynucleotide products (generally DNA products). In some embodiments of methods for generating labeled DNA products, at least one type of dNTP used is a labeled dNTP. In other embodiments of methods for generating labeled DNA products, a labeled composite primer is used.

The invention also provides methods which employ (usually, analyze) the products of the amplification methods of the invention, such as detection of sequence alteration(s) (e.g., genotyping, nucleic acid mutation detection, analysis of splice variants, and the like); determining presence or absence of a sequence of interest; quantifying a sequence of interest; gene expression profiling; subtractive hybridization; preparation of subtractive hybridization probe; differential amplification; preparation of libraries (including genomic, cDNA and differential expression libraries); preparation of an immobilized nucleic acid (which can be a nucleic acid immobilized on a microarray, preparing labeled probes for analysis on arrays (including high density arrays) for the detection and quantification of sequences of interest, including, for example, sequence determination, detecting sequence variation and genotyping; comparative genome hybridization; detection and/or identification of novel RNAs; and characterizing nucleic acids using the amplification nucleic acid products generated by the methods of the invention.

Any of the methods of the invention can be used to generate polynucleotide products that are suitable for characterization of a polynucleotide sequence of interest in a sample. In one embodiment, the invention provides methods for characterizing (for example, detecting (presence or absence) and/or quantifying) a polynucleotide sequence of interest comprising: (a) amplifying a target polynucleotide by any of the methods described herein; and (b) analyzing the amplification products. Step (b) of analyzing the amplification products can be performed by any method known in the art or described herein, for example by detecting and/or quantifying amplification products that are hybridized to a probe. These amplification products may or may not be labeled. Any of the methods of the invention can be used to generate polynucleotide (such as DNA) products that are labeled by incorporating labeled nucleotides and/or labeled composite primers into appropriate step(s) of the methods. These labeled products are particularly suitable for quantification and/or identification by methods known in the art, which include the use of arrays such as cDNA microarrays and oligonucleotide arrays.

In one aspect, the invention provides a method of characterizing a polynucleotide sequence of interest, comprising (a) amplifying a target polynucleotide by a method described herein to generate labeled polynucleotide products; and (b) analyzing the labeled polynucleotide products. In some embodiments, the step of analyzing polynucleotide products comprises determining amount of said products, whereby the amount of the polynucleotide sequence of interest present in a sample is quantified.

The amplification products can also serve as template for further analysis such as sequence analysis, polymorphism detection (including multiplex SNP detection) using, e.g., oligonucleotide ligation-based assays, analysis using Invader, Cleavase or limited primer extension, and other methods known in the art. For methods that generally require larger volumes of input material, the methods of the invention may be used to "pre" amplify a pool of polynucleotides to generate sufficient input material for subsequent analysis.

In another embodiment, the polynucleotide products can be analyzed by, for example, contacting them with at least one probe. In some embodiments, the at least one probe is provided as a microarray. The microarray can comprise at least one probe immobilized on a solid or semi-solid substrate fabricated from a material selected from the group consisting of paper, glass, ceramics, plastic, polypropylene, polystyrene, nylon, polyacrylamide, nitrocellulose, silicon, other metals, and optical fiber. A probe can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of determining a gene expression profile in a sample, the methods comprising (a) amplifying RNA template in a sample using any of the methods described herein; and (b) determining an amount of amplification products of each RNA sequence of interest in the sample, whereby the gene expression profile of the sample is determined. The invention further provides methods of determining a gene expression profile by determining an amount of amplification products of each RNA sequence of interest in a sample, the sample comprising multiple copies of RNA template amplified by any of the methods described herein, whereby the gene expression profile of the sample is determined.

Additionally, the invention also provides methods for archiving polynucleotide templates. Because the amplification methods of the invention provide representative amplification of the sequences of the template polynucleotide, amplified product produced by the instant methods may be used as an archival source for the original template polynucleotide. Accordingly, the invention provides methods for archiving a polynucleotide template by storing the amplification products produced by the methods of the invention. The archived amplification products may be analyzed as described herein, or may be subjected to further amplification in accordance with the methods of the invention.

In another aspect, the invention provides products (e.g., multiple copies of a template polynucleotide) produced by the methods disclosed herein.

The invention also provides compositions, kits, complexes, reaction mixtures and systems comprising various components (and various combinations of the components) used in the amplification methods described herein.

In another aspect, the invention provides compositions comprising any of the complexes (which are generally considered as intermediates with respect to the final amplification products) described herein.

In another aspect, the invention includes any one or more products (including intermediates) and compositions comprising the products (including intermediates) produced by any aspect of the methods of the invention.

In another aspect, the invention provides reaction mixtures (or compositions comprising reaction mixtures) which contain various combinations of components described herein.

In another aspect, the invention provides kits for conducting the methods described herein. These kits, in suitable packaging and generally (but not necessarily) containing suitable instructions, contain one or more components used in the amplification methods.

In another aspect, the invention provides systems for effecting the amplification methods described herein.

BRIEF DESCRIPTION OF THE DRAWINGS

FIG. 1 illustrates one embodiment of a composite primer useful in the methods of the present invention. As illustrated in the Figure, the composite primer comprises a DNA portion at its 3' end and an RNA portion at its 5' end. As discussed herein, it is also possible to employ a composite primer in which the 3' DNA portion is followed, in the direction of its 5', by an RNA portion, which is followed by a portion which is DNA.

FIG. 2 illustrates a composite primer that hybridizes to multiple sites on a template polynucleotide where differing portions of the composite primer are hybridized to template polynucleotide depending on the site at which it is hybridized.

FIG. 7 illustrates primer extension from composite primers and auxiliary primers that are hybridized at multiple sites on a template strand.

MODES FOR CARRYING OUT THE INVENTION

Figure 3:
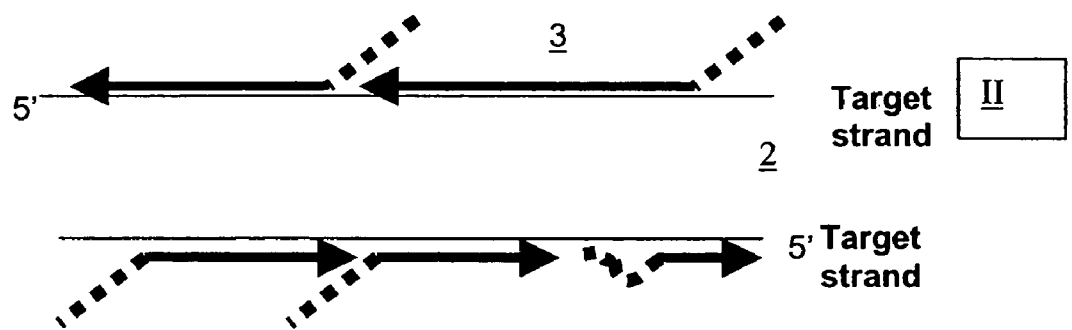
FIG. 3 illustrates primer extension from composite primers that are hybridized at multiple sites on a template strand, where a composite primer extension products is being displaced by primer extension from a composite primer hybridized at a downstream site on the template strand.

Overview of the Invention and its Advantages

The invention discloses novel methods, compositions and kits for global amplification. The methods provide for amplification using a composite primer that is capable of binding to multiple sites within template polynucleotide (e.g., mRNA or genomic DNA), whereby a large multiplicity of template polynucleotide sequences (for example, essentially all genomic DNA) is amplified. The methods are suitable for use with either DNA or RNA template. They generate polynucleotide (generally, DNA) products, which are readily suitable for a variety of uses including comparative genome hybridization, expression profiling, and multiple genotype determinations, e.g., by multiplex analysis by microarray technologies. The methods are amenable to automation and do not require thermal cycling. Thus, one of the major advantages of the methods of the invention is the ability to amplify an entire pool of sequences (or a subset thereof, depending on the desired extent of amplification), which is essential for application such as comparative genome hybridization, generation of cDNA libraries, generation of subtractive hybridization probes, and array based assays, including multiple genotype determinations.

The amplification methods of the invention involve composite primer random hybridization, primer extension and displacement of composite primer extension product by strand displacement, whereby a complex comprising a RNA-DNA heteroduplex is generated, followed by composite primer-dependent isothermal amplification using the complex as a substrate for further amplification, an aspect that permits rapid amplification and distinguishes the invention from other strand displacement amplification methods, such as MDA.

In one aspect, the methods of the invention involve two phases: (a) composite primer random hybridization to template polynucleotide, primer extension and displacement of composite primer extension product by strand displacement DNA synthesis, whereby a complex comprising a RNA/DNA partial heteroduplex is generated, and (b) composite primer-dependent single primer isothermal amplification using the complex comprising a RNA/DNA partial heteroduplex as a substrate for further amplification.

The methods generally comprise using specially-designed primers, generally a RNA/DNA composite primer, to randomly prime template polynucleotide (such as genomic DNA template, mRNA or noncoding RNA). By "randomly prime" or "random hybridization", as used herein, it is meant that the composite primer hybridizes to multiple sites within template polynucleotide. In some embodiments, an aspect of the invention is displacement of primer extension product from template polynucleotide(s) during primer extension by strand displacement DNA synthesis (e.g., by primer extension with a DNA polymerase having strand displacement activity) of primers hybridized at a downstream position(s) on the template.

Thus, the invention provides methods of incubating a reaction mixture, said reaction mixture comprising: (a) a polynucleotide template; (b) a composite primer; wherein the composite primer comprises an RNA portion and a 3' DNA portion, and wherein the composite primer is capable of hybridizing to a multiplicity of template polynucleotide sites; (c) a DNA-dependent DNA polymerase with strand displacement activity; and (d) an RNA-dependent DNA polymerase; wherein the incubation is under conditions that permit composite primer random hybridization, primer extension and displacement of the primer extension product from template polynucleotide, whereby a population of intermediate complexes are generated that generally includes (a) copies of template polynucleotide and/or copies of the complement of polynucleotide sequence appended (via extension) to composite primer sequences; and (b) copies of template polynucleotide and copies of the complement of template polynucleotide appended (via extension) to the complement of composite primer sequences. The intermediate complexes may be double-stranded or may be partially double stranded. By virtue of the presence of composite primer sequences in the intermediate complexes, the complexes comprise a RNA/

DNA heteroduplex partial heteroduplex. The RNA portion of the RNA/DNA partial heteroduplex generally is introduced by the RNA portion of the composite primer, and the DNA portion of the heteroduplex is made of the complement of the RNA portion of the composite primer. For simplicity, this population of intermediate complexes is termed "a complex comprising an RNA/DNA partial heteroduplex."

Generally, the composite primer comprises at least a 3' DNA portion that is capable of randomly priming template polynucleotide. Thus, and as the description makes clear, reference to a primer that hybridizes to a sequence encompasses embodiments in which at least a portion of the primer is hybridized, embodiments in which two (or more portions) of the primer are hybridized (separated by unhybridized (looped out) portions of the primer), and embodiments in which the entire primer is hybridized.

The complex comprising a RNA/DNA partial heteroduplex is substrate for further amplification as follows: an enzyme which cleaves RNA from an RNA/DNA hybrid (such as RNase H) cleaves RNA sequence from the hybrid, leaving a 3' single stranded DNA sequence available for binding by a composite primer (which may or may not be the same as the first composite primer). Extension of a bound composite primer by DNA-dependent DNA polymerase produces a primer extension product, which displaces the previously bound cleaved first primer extension product, whereby polynucleotide (generally, DNA) product accumulates. It is understood that amplified product generally is a mixture of sense and antisense copies of a given template polynucleotide. For example, if the template polynucleotide is double stranded DNA, the amplification product will correspond to each strand. If the template polynucleotide is single stranded, amplification product will generally be produced that is the copy of template polynucleotide (sense copy) and the complement of the template polynucleotide (antisense copy).

The methods disclosed herein are applicable to the amplification of any target polynucleotide, including both DNA (e.g., genomic DNA) and RNA (e.g., mRNA and ribosomal RNA) targets. As is evident from the description and shown in the example, the methods of the invention are composite-primer dependent. That is, amplification is not observed in the absence of the composite primer.

In another aspect of the invention, auxiliary primers are present in the reaction mixture comprising template polynucleotide, composite primer, DNA-dependent DNA polymerase and RNA-dependent DNA polymerase. As used herein, "auxiliary primers" refers to a population of random and/or partially randomized primers. Inclusion of a population of random primers during the amplification is believed to enhance the efficiency of production of and/or global (template-wide, e.g., providing representative amplification of the template, whether the template is DNA or RNA) coverage of the amplification product.

In certain aspects, global amplification of genomic DNA is exemplified herein. It is understood, however, that the amplification methods of the invention are suitable for amplification of any pool or subset (or polynucleotides representing a significant proportion of a pool or subset, depending on desired extent of amplification) of polynucleotides.

Accordingly, in one aspect, the invention provides methods for amplification of a template polynucleotide, said methods comprising: (a) incubating a reaction mixture, said reaction mixture comprising: (i) a template polynucleotide; (ii) a first primer, wherein the first primer is a composite primer that is hybridizable to a multiplicity of template polynucleotide sites, wherein the composite primer comprises an RNA portion and a 3' DNA portion; (iii) a DNA-dependent DNA polymerase; and (iv) an RNA-dependent DNA polymerase (which may be present as a separate enzyme or as an enzyme comprising both DNA-dependent DNA polymerase and RNA-dependent DNA polymerase activities); wherein the incubation is under conditions that permit composite primer random hybridization, primer extension and displacement of the primer extension product from template polynucleotide, whereby a complex comprising an RNA/DNA partial heteroduplex is generated; and (b) incubating a reaction mixture, said reaction mixture comprising (i) the reaction products generated according to step (a) (or an aliquot thereof); (ii) a composite primer (which may be the same as the first primer, or may be a different primer), wherein the composite primer comprises an RNA portion and a 3' DNA portion; (iii) an DNA-dependent DNA polymerase; and (iv) an agent (such as an enzyme) that cleaves RNA from an RNA/DNA hybrid; wherein the incubation is under conditions that permit primer hybridization, primer extension, RNA cleavage from an RNA/DNA heteroduplex, and displacement of the primer extension product (i.e., strand displacement DNA synthesis) from the complex of (a) when its RNA is cleaved and another composite primer binds to the template and is extended, whereby multiple copies of a polynucleotide (generally, DNA) amplification product are generated. In some embodiments, the reaction mixture of step (b) comprises the reaction mixture according to step (a) (or an aliquot thereof). In other embodiments, step (b) is initiated by the addition of an agent that cleaves RNA from an RNA/DNA heteroduplex (such as RNase H), and optionally, a DNA-dependent DNA polymerase, to the reaction mixture of step (a). In some embodiments, the reaction mixture of step (a) and/or (b) further comprises auxiliary primers.

In another aspect, the invention provides methods for amplification of a template polynucleotide by incubating a reaction mixture, said reaction mixture comprising: (a) a complex of a first primer extension product and a second primer extension product, wherein the first primer extension product is generated by extension of a randomly primed first primer hybridized to target polynucleotide with a DNA polymerase, wherein the first primer is a composite primer comprising an RNA portion and a 3' DNA portion, wherein the first primer is capable of hybridizing to a multiplicity of template polynucleotide sites, and wherein the second primer extension product is generated by extension of a second primer hybridized to the first primer extension product; (b) a composite primer that is hybridizable to the second primer extension product, wherein the composite primer comprises an RNA portion and a 3' DNA portion; (c) a DNA-dependent DNA polymerase; and (d) an enzyme that cleaves RNA from an RNA/DNA hybrid; wherein the incubation is under conditions that permit primer hybridization, primer extension, RNA cleavage from an RNA/DNA heteroduplex, and displacement of composite primer from the complex of step (a) when its RNA is cleaved and another composite primer binds and is extended, whereby multiple copies of a polynucleotide amplification product are generated. In some embodiments, the first primer extension product and/or the second primer extension product are generated in the presence of auxiliary primers.

In another aspect of the invention wherein the template polynucleotide is RNA, template RNA is cleaved following random composite primer hybridization and primer extension. Template RNA can be cleaved using methods well-known in the art, including cleavage with an agent (such as an enzyme, such as RNase H) that cleaves RNA from an RNA/DNA hybrid, cleavage resulting from heat treatment, and cleavage due to chemical treatment (e.g., treatment under alkaline conditions). In some embodiments, the invention provides methods of incubating a reaction mixture, said reaction mixture comprising: (a) an RNA template; (b) a composite primer; wherein the composite primer comprises an RNA portion and a 3' DNA portion; and wherein the composite primer is capable of hybridizing to a multiplicity of sites in template RNA; (c) a DNA-dependent DNA polymerase; (d) an RNA-dependent DNA polymerase; and (e) an enzyme capable of cleaving RNA from an RNA/DNA hybrid; wherein the incubation is under conditions that permit composite primer random hybridization, primer extension, template RNA cleavage from an RNA/DNA heteroduplex, whereby a complex comprising an RNA/DNA partial heteroduplex is generated. The complex comprising an RNA/DNA partial heteroduplex is the substrate for further amplification as described above (i.e., single primer isothermal amplification). In some embodiments, an auxiliary primer is included in the reaction mixture.

Template polynucleotide may also be prepared from RNA template by synthesis of cDNA. cDNA synthesis may be accomplished using standard methods, such as priming with random primers (e.g., random hexamer deoxyoligonucleotides) and primer extension with a RNA-dependent DNA polymerase (e.g., reverse transcriptase) in the presence of dNTPs and appropriate reaction conditions (e.g., temperature, pH and ionic conditions). Only the first strand cDNA synthesis need be performed, as first strand cDNA synthesis will produce a DNA polynucleotide that can be amplified in accordance with the methods of the invention.

The methods of the invention include methods using the amplification products (so-called "applications"). The invention also provides methods which employ (usually, analyze) the products of the amplification methods of the invention, such as methods of nucleic acid mutation detection (including methods of genotyping), determining the presence or absence of a sequence of interest, quantitating a sequence of interest, preparation of an immobilized nucleic acid, comparative genomic hybridization, discovery of novel nucleic acid sequences, and characterizing nucleic acids using the amplified nucleic acid products generated by the methods of the invention.

Any of the methods of the invention can be used to generate polynucleotide products that are suitable for characterization of a polynucleotide sequence of interest in a sample. In one embodiment, the invention provides methods for characterizing (for example, detecting (presence or absence) and/or quantifying) a polynucleotide sequence of interest comprising: (a) amplifying a target polynucleotide by any of the methods described herein; and (b) analyzing the amplification products. Step (b) of analyzing the amplification products can be performed by any method known in the art or described herein, for example by detecting and/or quantifying amplification products that are hybridized to a probe. These amplification products may or may not be labeled. Any of the methods of the invention can be used to generate polynucleotide (such as DNA) products that are labeled by incorporating labeled nucleotides and/or labeled composite primers into appropriate step(s) of the methods. These labeled products are particularly suitable for quantification and/or identification by methods known in the art, which include the use of arrays such as cDNA microarrays and oligonucleotide arrays.

The invention provides methods to characterize (for example, detect presence or absence of and/or quantify) an polynucleotide sequence of interest by generating polynucleotide products using amplification methods of the invention, and analyzing the products by detection/quantification methods such as those based on array technologies or solution phase technologies. These amplification products may be labeled or unlabeled.

The methods of the invention may be used to amplify a pool of polynucleotides (or polynucleotides representing a significant proportion of a pool, depending on desired extent of amplification) to generate sufficient input material for subsequent analysis. Thus, and as is described herein, amplification products can also serve as template for further analysis such as sequence, polymorphism detection (including multiplex SNP detection) using, e.g., oligonucleotide ligation-based assays, analysis using Invader, Cleavase or limited primer extension, and the like. Amplification product may also serve as template for further amplification by the methods of the invention or other amplification method known in the art.

In yet another embodiment, the invention provides methods for immobilizing nucleic acids, including methods for generating microarrays of nucleic acids, using amplification products of the amplification methods of the invention.

In another embodiment, the invention provides methods of generating cDNA libraries, methods of generating subtractive hybridization probes, and methods of generating subtractive hybridization libraries.

Advantages of the Invention

Various methods for global amplification of nucleic acids have been developed. PCR-based methods, such as PEP, may generate non-specific amplification artifacts, give incomplete coverage of loci, or generate DNA product of insufficient length that cannot be used in many applications. PCR-based methods also suffer from the propensity of the PCR reaction to generate products that are preferentially amplified, and thus resulting in biased representation of genomic sequences in the products of the amplification reaction. Also, PCR-based methods require cumbersome thermal cycling.

Additionally, a number of methods for the detection and quantification of gene expression levels have been developed in recent years. For example, microarrays, in which either defined cDNAs or oligonucleotides are immobilized at discrete locations on, for example, solid or semi-solid substrates, or on defined particles, enable the detection and/or quantification of the expression of a multitude of genes in a given specimen. Using these previously known methods to detect presence of absence of and/or quantify multiple RNA species in a sample, which in turn is used as a measure of gene expression profiling, generally requires direct labeling of cDNA, which requires a large amount of input total RNA. Thus, when using total RNA preparations from a given cell or tissue sample to analyze mRNA, the analysis of gene expression in the sample using methods such as arrays requires a substantial amount of input RNA, which generally ranges from 50 to 200 µg. Similarly, 2 to 5 µg of mRNA purified from a total RNA preparation would generally be required for a single analysis of gene expression profiling using array technologies. This is a clear limitation of methods such as those based on array technology, insofar as the number of cells, or size of tissue specimen required is very large, and these cells or tissue specimens are often scarcely available for testing or are too precious. This limitation is especially severe in the study of clinical specimens, where the cells to be studied are rare and/or difficult to cultivate in vitro, and in high throughput screening of libraries of effector molecules. Also, previous transcription-based methods of amplification of mRNA (described in, for example, Lockhart et al, Nature Biotechnology (1996), 14, 1675-1680); van Gelder et al., U.S. Pat. No. 5,716,785), are limited to the amplification efficiency of DNA-dependent RNA polymerases and some of these methods require multiple steps. Moreover, the process by which the polymerase promoter sequence is incorporated is prone to result in non-specific amplification.

The methods of the invention offer the ability to efficiently amplify template polynucleotides (including both RNA and DNA). Thus, the utility of detection/quantification methods which ca be used with the amplification products of the invention, such as those based on array technology, real time PCR, quantitative TaqMan, quantitative PCR using molecular beacons, and the like, should be greatly enhanced.

The methods of the invention do not require thermocycling and all of the steps can be performed isothermally, although the various steps may be carried out a different temperatures. This feature provides numerous advantages, including facilitating automation and adaptation for high through-put procedures. The isothermal reaction is generally faster than that afforded by thermal cycling, and is suitable for performing the methods of the invention in miniaturized devices.

The ability to efficiently amplify pools of template polynucleotide sequences (such as genomic DNA) under conditions that will generally not alter the representation of the nucleic acid sequences in the starting sample, will greatly enhance the utility of the detection/quantification methods such as those based on the powerful array technology.

The ability to efficiently amplify RNA using the random initiation of replication according the methods of the invention provides means for representing all sequences in the pool of sequences (or representing a significant proportion of a pool depending on desired extent of the amplification) in the sample, for example, sequences representing the full length of mRNA species in a sample. The methods of the invention do not rely on oligo-dT primers (to bind the poly-A tail of mRNA) to initiate amplification; thus, the methods may be used to amplify non-poly-A tailed RNAs, such as noncoding RNAs and RNAs of non-eukaryotic species. The methods of the invention do not require prior knowledge of the sequences in the sample and are thus suitable for discovery of novel transcripts, even when present in low abundance and/or representing non-coding transcripts. The ability to efficiently amplify RNA under conditions that will generally not alter the representation of the nucleic acid sequences in the preparation, will greatly enhance the utility of the detection/quantification methods such as those based on the powerful array technology.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sam brook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

Definitions

A "template," "template strand," "template polynucleotide," "template DNA," "target sequence," "target nucleic acid," or "target DNA," "target polynucleotide," "template RNA," or "target RNA," as used herein, is a polynucleotide for which amplification is desired. The template polynucleotide can comprise DNA or RNA. The template sequence may be known or not known, in terms of its actual sequence. Generally, the terms "target," "template," and variations thereof, are used interchangeably.

"Amplification," or "amplifying", as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during amplification. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3$H, $^{35}$S, $^{32}$P, $^{33}$P, $^{125}$I, or $^{14}$C), enzymes (e.g., LacZ, horseradish peroxidase, alkaline phosphatase, ), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. Oligonucleotides in the invention include the composite primer and auxiliary primer. The terms "oligonucleotide" and "polynucleotide" are not mutually exclusive. The description above for polynucleotides is equally and fully applicable to oligonucleotides.

A "primer," as used herein, refers to a nucleotide sequence, generally with a free 3'-OH group, that hybridizes with a template sequence (such as a target polynucleotide, target DNA, or a primer extension product) and is capable of promoting polymerization of a polynucleotide complementary to the template. A "primer" can be, for example, an oligonucleotide.

"Auxiliary primers" as used herein, are a population of primers comprising randomized and/or partially-randomized sequences. Auxiliary primers are a polynucleotide as described herein, though generally, auxiliary primers are made of DNA. Random primers are known in the art and are commercially available. An example of auxiliary primers is the population of randomized hexamer primers shown in Example 1.

To "inhibit" is to decrease or reduce an activity, function, and/or amount as compared to a reference.

By "randomly prime" or "random hybridization", as used herein, it is meant that the composite primer hybridizes to multiple sites within the template polynucleotide.

As used herein, "complex comprising an RNA/DNA partial heteroduplex" generally refers to a population of intermediate complexes that generally includes (a) copies of template polynucleotide and/or copies of the complement of template polynucleotide sequence appended to composite primer sequences; and (b) copies of template polynucleotide and/or copies of the complement of template polynucleotide appended to the complement of composite primer sequences. By virtue of the presence of composite primer sequence in the intermediate complexes, the complexes comprise at least a RNA/DNA partial heteroduplex. The RNA portion of the partial heteroduplex generally is introduced (via extension) by the RNA portion of the composite primer, and the DNA portion of the partial heteroduplex comprises the complement of the RNA portion of the composite primer. As discussed herein, the complex comprising an RNA/DNA partial heteroduplex functions as a substrate for further amplification during the single primer isothermal amplification phase of the methods. Generally, RNA in the RNA/DNA partial heteroduplex is cleaved, generating a 3' single stranded portion with sequences that are complementary to RNA in a composite primer (and thus forming a binding site for a composite primer). Thus, reference to "a complex comprising a 3' single stranded portion" generally refers to the complex comprising an RNA/DNA partial heteroduplex when its RNA is cleaved.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a complex of composite primer extension product and second composite primer extension product, as described herein.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 or more contiguous nucleotides.

A region, portion, or sequence which is "adjacent" to another sequence directly abuts that region, portion, or sequence. For example, an RNA portion which is adjacent to a 5' DNA portion of a composite primer directly abuts that region.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, and/or strand extension.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, transversion, deletion or insertion. Single nucleotide polymorphism (SNP) is also a sequence mutation as used herein.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined locations on a substrate. Arrays are formed on substrates fabricated with materials such as paper, glass, plastic (e.g., polypropylene, nylon, polystyrene), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767-773; Pease et al., *Proc. Natl. Acad. Sci. U.S.A.* (1994), 91:5022-5026; Lockhart et al., *Nature Biotechnology* (1996), 14:1675; U.S. Pat. Nos. 5,578,832; 5,556,752; and 5,510,270); (ii) spotting/printing at medium to low-density (e.g., cDNA probes) on glass, nylon or nitrocellulose (Schena et al, *Science* (1995), 270:467-470, DeRisi et al, *Nature Genetics* (1996), 14:457-460; Shalon et al., *Genome Res.* (1996), 6:639-645; and Schena et al., *Proc. Natl. Acad. Sci. U.S.A.* (1995), 93:10539-11286); (iii) by masking (Maskos and Southern, *Nuc. Acids. Res.* (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 50, more preferably from about 10 to about 40, even more preferably from about 20 to about 30 nucleotides.

"Absent" or "absence" of product, and "lack of detection of product" as used herein includes insignificant, or de minimus levels, generally due to lack of significant accumulation of product.

In accordance with well established principles of patent law "comprising" means "including."

Amplification Methods of the Invention

The following are examples of the amplification methods of the invention. It is understood that various other embodiments may be practiced, given the general description provided above. For example, reference to using a composite primer means that any of the composite primers described herein may be used.

Amplification Using a Composite Primer that Hybridizes to a Multiplicity of Template Polynucleotide Sites The invention provides methods for global amplification using a composite primer that is capable of binding to multiple sites within template polynucleotide, including DNA and RNA template polynucleotides.

Generally, the methods of the invention involve two phases. (a) composite primer random hybridization, primer extension and displacement of composite primer extension product by strand displacement, whereby a complex comprising a RNA/DNA partial heteroduplex is generated, and (b) composite-primer dependent single primer isothermal amplification.

Thus, the methods of the invention work as follows: (a) incubating a reaction mixture, said reaction mixture comprising: (i) a template polynucleotide; (ii) a first primer, wherein the first primer is a composite primer that is hybridizable to a multiplicity of template polynucleotide sites, wherein the composite primer comprises an RNA portion and a 3' DNA portion; (iii) a DNA-dependent DNA polymerase; and (iv) an RNA-dependent DNA polymerase (which may be present as a separate enzyme or as an enzyme comprising both DNA-dependent DNA polymerase and RNA-dependent DNA polymerase activities); wherein the incubation is under conditions that permit composite primer random hybridization, primer extension and, in some embodiments, displacement of the primer extension product from template polynucleotide, whereby a complex comprising an RNA/DNA partial heteroduplex is generated; and (b) incubating a reaction mixture, said reaction mixture comprising (i) the reaction products generated according to step (a) (or an aliquot thereof); (ii) a composite primer (which may be the same as the first primer or may different from the first primer); (iii) an DNA-dependent DNA polymerase; and (iv) an agent (such as an enzyme) that cleaves RNA from an RNA/DNA hybrid; wherein the incubation is under conditions that permit primer hybridization, primer extension, RNA cleavage from an RNA/DNA heteroduplex, and displacement of the primer extension product when its RNA is cleaved and another composite primer binds to the template and is extended, whereby multiple copies of a polynucleotide (generally, DNA) amplification product are generated. In some embodiments, the reaction mixture of step (b) comprises the reaction mixture according to step (a) (or an aliquot thereof). In other embodiments, step (b) is initiated by the addition of an agent that cleaves RNA from an RNA/DNA heteroduplex (such as RNase H) to the reaction mixture of step (a). In embodiments in which the template polynucleotide is RNA, the reaction mixture of step (a) further comprises an agent (such as an enzyme) that that cleaves RNA from an RNA/DNA heteroduplex.

(a) Composite Primer Random Hybridization, Primer Extension and Displacement of Composite Primer Extension Product by Strand Displacement The methods generally comprise using specially-designed primers, generally a RNA/DNA composite primer. In a first phase of the amplification methods, composite primer is used to randomly prime template polynucleotide (such as genomic DNA). By "randomly prime" or "random hybridization", as used herein, it is meant that the composite primer hybridizes to multiple sites within template polynucleotide. We have discovered that certain composite primers bind a multiplicity of sites within template polynucleotide (generally, under conditions promoting random primer hybridization) and are thus particularly suitable for use in the methods of the invention. Generally, suitable composite primers show partial homology to a multiplicity of template nucleic acid sequences, particularly in the 3' sequences of the composite primer, and thus, the composite primer comprises at least a 3' DNA portion that is capable of randomly priming template polynucleotide (particularly under conditions permitting random primer hybridization). Selection and design of composite primers is described further below.

Various embodiments of the composite primer and used in the methods of the invention are described herein. For example, FIG. 1 illustrates one embodiment of a composite primer useful in the methods of the present invention. As illustrated in the Figure, the composite primer comprises a DNA portion at its 3' end and an RNA portion at its 5' end. As discussed herein, it is also possible to employ a composite primer in which the 3' DNA portion is followed, in the direction of its 5', by an RNA portion, which is followed by a portion which is DNA. The length of each of these sections is generally determined for maximum efficiency of the amplification. In some embodiments, the composite primer that hybridizes to target polynucleotide and the composite primer used during single primer isothermal amplification are the same. In some embodiments, the composite primer that hybridizes to target polynucleotide and the composite primer used during single primer isothermal amplification are different.

Reference to a primer that binds (hybridizes to) a sequence (or template) encompasses embodiments in which at least a portion of the primer is hybridized, as well as those embodiments in which an entire primer is hybridized. Thus, and as the description makes clear, reference to a primer that hybridizes to a sequence encompasses embodiments in which at least a portion of the primer is hybridized as well as embodiments in which two (or more portions) of the primer are hybridized, separated by unhybridized (looped out) portions of the primer, and embodiments in which the entire primer is hybridized. For example, FIG. 2 illustrates a single composite primer that hybridizes to multiple positions on a template polynucleotide where differing portions of the composite primer are hybridized to template polynucleotide depending on the site (sequence) at which it is hybridized. Thus, according to the methods of the invention, only a portion of the 3'-end of the composite primer must be hybridized in order for initiation of primer extension by DNA polymerase. In some embodiments, for example, only 2, 3, 4, 5, 6, 7, 8 or more nucleotides of the 3' end of the primer need to hybridize in order for primer extension to be initiated. It is understood that hybridization of the 3'-most portion of the composite primer may be stabilized to various extents by further hybridization of another portion of the primer (with or without looping out of intervening primer portions). A DNA polymerase can be included during primer hybridization to enhance (e.g., stabilize) hybridization of composite primer by initiation of primer extension, and thus, stabilization of primer hybridization.

Random hybridization of the composite primer to template polynucleotide generally occurs under conditions permitting random (nonspecific) primer hybridization. Such conditions are well known in the art and include: decreased stringency during primer hybridization and/or primer extension (including reduced temperature and/or buffer conditions of reduced stringency); composite primer selection and/or design (discussed further herein); and composite primer and template concentration. It is understood that stringency of hybridization, composite primer selection and/or primer concentration may be used to control the frequency of composite primer hybridization, and thus to control coverage and/or representation of template sequences in amplification product. As noted above, an aspect of the invention is displacement of intervening primer extension product during primer extension of composite primers hybridized at downstream position(s) on the template, whereby primer extension products are displaced from template polynucleotide. Preferably, a DNA polymerase is used that possesses stand displacement activity.

Composite primer random hybridization, primer extension and displacement of primer extension product by strand displacement results in generation of a multiplicity of complexes comprising a RNA/DNA partial heteroduplex. The complexes comprise (a) copies of template polynucleotide and/or copies of the complement of polynucleotide sequence appended (via extension) to composite primer sequences; and (b) copies of template polynucleotide and copies of the complement of template polynucleotide appended (via extension) to the complement of composite primer sequences. Generally, the RNA portion of the complex is introduced by the composite primer.

In some embodiments, generation of complexes comprising a RNA/DNA partial heteroduplex involves the following steps: (i) formation of a composite primer extension product; and (ii) formation of a second primer extension product by primer extension along the first primer extension product. For example, in some embodiments, complex comprising an RNA/DNA partial heteroduplex is generated as follows: following random hybridization of the composite primer at multiple sites on template polynucleotide strands, a DNA polymerase extends the composite primer along the template strand generating a composite primer extension product that is complementary to the polynucleotide template strand. Primer extension extends to and displaces strands being extended from primers hybridized at upstream sites on the template. Thus, as noted above, an aspect of the invention is displacement of intervening primer extension product during primer extension of composite primers hybridized at downstream site(s) on the template, whereby composite primer extension products are displaced from template polynucleotide. FIG. 3 illustrates primer extension from composite primers that are hybridized at multiple sites on a template strand, where a composite primer extension products is being displaced by primer extension from a composite primer hybridized at a downstream site(s) on template strand.

Figure 4:
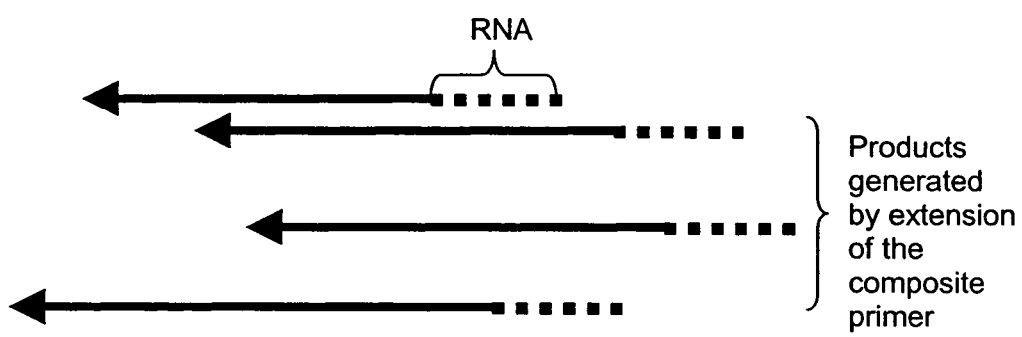
FIG. 4 shows a collection of composite primer extension products comprising composite primer 1 linked (via extension) to sequences corresponding to a multiplicity of target polynucleotide sequences.

Displaced composite primer product comprises the composite primer sequence at the 5' end, including the 5' RNA portion. Although for convenience, reference is made only to "a" composite primer extension product, it is understood that a multiplicity of composite primer extension products are generated the complement of a multiplicity of template polynucleotide sequences appended (via extension) to the sequence of the composite primer. FIG. 4 shows a collection of composite primer extension products comprising composite primer 1 linked (by extension) to sequences comprising the complement of a multiplicity of target polynucleotide sequences.

Figure 5:
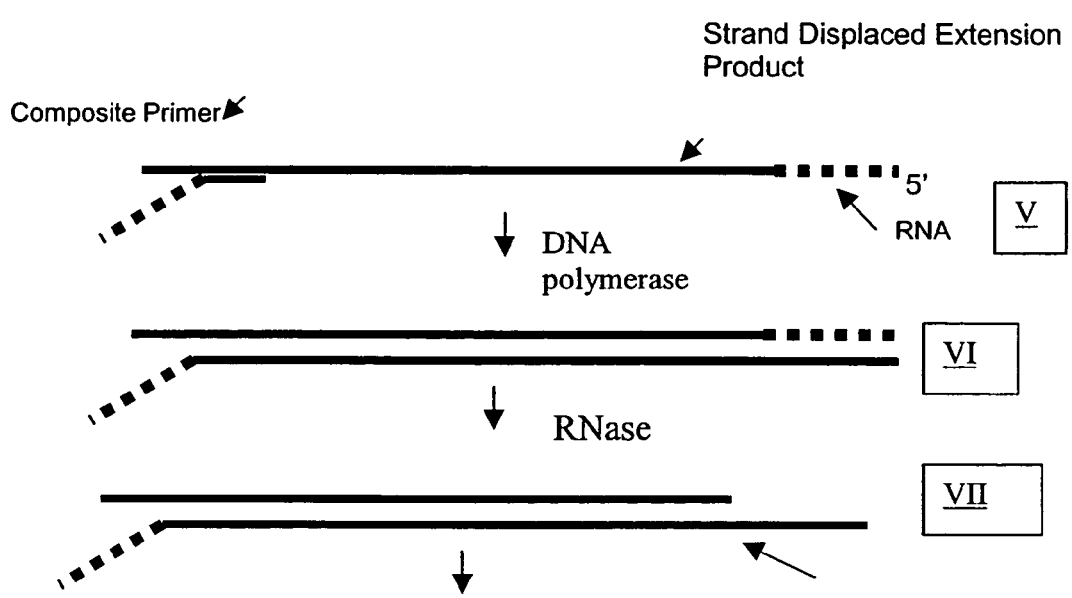
FIG. 5 shows generation of second primer extension product that is randomly primed by the composite primer.

Using displaced composite primer extension product as a template, a second primer extension product complementary to the first primer extension product is generated by extension by a DNA-dependent DNA polymerase along the DNA portion of the composite primer extension product, and extension by a RNA-dependent DNA polymerase along the 5' RNA portion of the composite primer extension product, generating a double stranded complex comprising a RNA/DNA complex at the end. Generation of second primer extension product may be random primed using the composite primer, as depicted in FIG. 5. Alternatively, second primer extension product may be primed by the 3' end of a different composite primer extension product. Additional embodiments in which second strand production is primed by exogenous (added) primers and/or by fragments of template RNA (endogenous primers) are described below.

Figure 6:
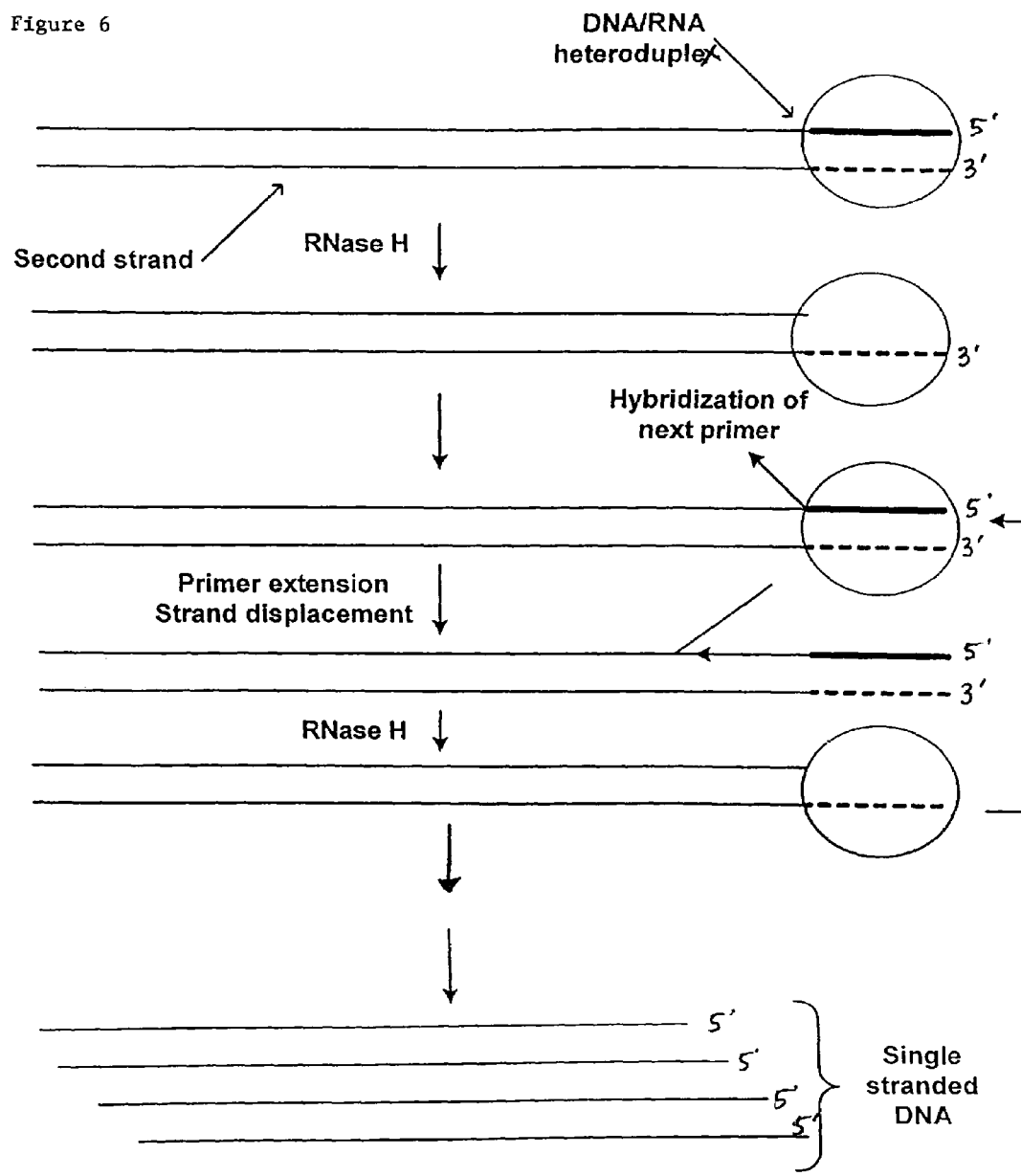
FIG. 6 shows single primer isothermal amplification using the complex comprising a RNA/DNA partial heteroduplex as a template for further composite-primer dependent amplification.

(b) Single Primer Isothermal Amplification Using a Complex Comprising an RNA/DNA Partial Heteroduplex as a Template In a second phase of the methods, termed single primer isothermal amplification, the complex comprising an RNA/DNA partial heteroduplex is a substrate for further amplification as follows: an enzyme which cleaves RNA sequence from an RNA/DNA hybrid (such as RNase H) cleaves RNA from the partial heteroduplex, leaving a partially double stranded polynucleotide complex comprising a 3' single stranded DNA sequence. The 3' single stranded sequence (formed by cleavage of RNA in the complex comprising an RNA/DNA partial heteroduplex) is generally the complement of the RNA in the composite primer, and thus forms a specific binding site for a composite primer (which may or may not be the same as the first composite primer). Extension of a bound composite primer by a DNA-dependent DNA polymerase produces a primer extension product, which displaces the previously bound cleaved primer extension product, whereby polynucleotide (generally, DNA) product accumulates. See, for example, U.S. Pat. Nos. 6,251,639 and 6,692,918. FIG. 6 shows amplification of DNA product using a composite primer and a complex comprising a RNA/DNA partial heteroduplex as a template for further amplification.

Amplification using a complex comprising an RNA/DNA partial heteroduplex as a template for further amplification (also termed single primer isothermal amplification) generally occurs under conditions permitting composite primer hybridization, primer extension, cleavage of RNA from an RNA/DNA hybrid and strand displacement. In so far as the composite primer hybridizes to the 3' single stranded portion (of the partially double stranded polynucleotide which is formed by cleaving RNA in the complex comprising an RNA/DNA partial heteroduplex) comprising, generally, the complement of at least a portion of the composite primer sequence, composite primer hybridization may be under conditions permitting specific hybridization. Thus, in some embodiments, the reactions conditions permit stringent hybridization (i.e., hybridization of sequences that are generally complementary). As is evident from the description herein, in other embodiments, the reaction conditions are less stringent (i.e., permit hybridization of sequences that are less than fully complementary).

Generally, the methods of the invention result in amplification of a multiplicity, a large multiplicity, or a very large multiplicity of template polynucleotide sequences. In some embodiments, essentially all of the template polynucleotide present in the initial sample (e.g., all of the mRNA or all of the genomic DNA) is amplified. In other embodiments, at least 50, at least 100, at least 200, at least 300, or more distinct sequences (such as a gene or other subsegment of a polynucleotide, a marker (such as a SNP or other polymorphism) are amplified, as assessed, e.g., by analysis of marker sequences known to be present in the template sample under analysis, using methods known in the art. Template polynucleotide sequences that are amplified may be present on the same polynucleotide (e.g., a chromosome or portion of a chromosome for genomic DNA template or on the same RNA for RNA template) or on different template polynucleotides (e.g., different chromosome or portions of chromosomes for DNA template, or different RNAs for RNA template). Although, amplification of genomic DNA is exemplified herein, it will be understood by those of skill in the art, however, that the global amplification methods of the invention are suitable for amplification of any pool or subset of polynucleotides.

For convenience, reference is made to a polynucleotide (generally, DNA) product. It is understood that amplified product generally is a mixture of sense and antisense copies of a given template polynucleotide. For example, if the template polynucleotide is double stranded DNA, the amplification product will correspond to each strand. If the template polynucleotide is single stranded (e.g., RNA or single stranded DNA), amplification product will generally be produced that is the copy of template polynucleotide (sense copy) and the complement of the template polynucleotide (antisense copy). The amplification product of different senses can be annealed to form a double stranded (or partially double stranded) complex, or can be prevented from annealing (or subsequently denatured) to produce a mixture of single stranded amplification products. The amplified products may be of differing lengths.

As is evident from the description and shown in the example, the methods of the invention are composite-primer dependent. That is, amplification is not observed in the absence of the composite primer.

As illustrated in these embodiments, all steps are isothermal (in the sense that thermal cycling is not required), although the temperatures for each of the steps may or may not be the same. It is understood that various other embodiments may be practiced, given the general description provided above. For example, as described and exemplified herein, certain steps may be performed as temperature is changed (e.g., raised, or lowered).

For simplicity, the methods of the invention are described as two distinct steps or phases, above. It is understood that the two phases may occur simultaneously in some embodiments (for example, if the enzyme that cleaves RNA from RNA/DNA hybrid is included in the first reaction mixture). In other embodiments, step (b) may be initiated by addition of an enzyme that cleaves RNA from an RNA/DNA hybrid (e.g., ribonuclease, such as RNase H), and optionally, a DNA-dependent DNA polymerase, as shown in Example 1. In this embodiment, addition of an enzyme that cleaves RNA from an RNA/DNA hybrid permits further amplification using the complex comprising an RNA/DNA partial heteroduplex as a template (i.e., step (b), above). It is understood, however, that primer extension (and strand displacement) along template polynucleotide strand from random primed composite primer(s) may continue during single primer isothermal amplification.

Although generally only one composite primer is described above, it is further understood that the amplification methods may be performed in the presence of two or more different composite primers that randomly prime template polynucleotide. In addition, the amplification polynucleotide products of two or more separate amplification reactions conducted using two or more different composite primers that randomly prime template polynucleotide can be combined. In addition, it is understood that different composite primers can be used in step (a) (i.e., random priming of template polynucleotide) and step (b) (i.e., single primer isothermal amplification). In this instance, the different composite primer comprises sequences hybridizable to the 3' single stranded DNA portion of the partially double stranded complex (which is generated by cleaving RNA from the complex comprising a RNA/DNA partial heteroduplex). Generally, the second composite primer comprises sequences overlapping with the first composite primer.

Amplification Using a Composite Primer that Hybridizes to a Multiplicity of Template Polynucleotide Sites and Auxiliary Primers In another aspect of the invention, auxiliary primers are present in the reaction mixture comprising template polynucleotide, composite primer, DNA-dependent DNA polymerase and RNA-dependent DNA polymerase. As used herein, "auxiliary primers" refers to a population of random or partially randomized primers. An example of auxiliary primers is the random hexamer primers used in Example 1. Inclusion of auxiliary primers (i.e., population of different random primers) during the amplification is believed to enhance the efficiency of production of and/or target coverage of the amplification product.

In some embodiments, the methods of the invention work as follows: (a) incubating a reaction mixture, said reaction mixture comprising a composite primer as described herein; auxiliary primers; a template polynucleotide, DNA-dependent DNA polymerase, and RNA-dependent DNA polymerase (which may be present as a single enzyme comprising both activities), wherein the incubation is under conditions suitable for random composite primer hybridization, auxiliary primer hybridization, primer extension, and strand displacement, whereby a complex comprising an RNA/DNA partial heteroduplex is generated; and (b) incubating a reaction mixture, said reaction mixture comprising the reaction products from step (a) (or an aliquot thereof); a composite primer (which may be the same as the composite primer of step (a) or may be a different composite primer); a DNA-dependent DNA polymerase; optionally, auxiliary primers; and an enzyme that cleaves RNA from a RNA/DNA hybrid; wherein the incubation is under conditions that permit primer hybridization, primer extension, RNA cleavage from an RNA/DNA heteroduplex, and displacement of the primer extension product from the complex when its RNA is cleaved and another composite primer binds to the template and is extended, whereby multiple copies of a polynucleotide template sequence are generated.

Figure 8:
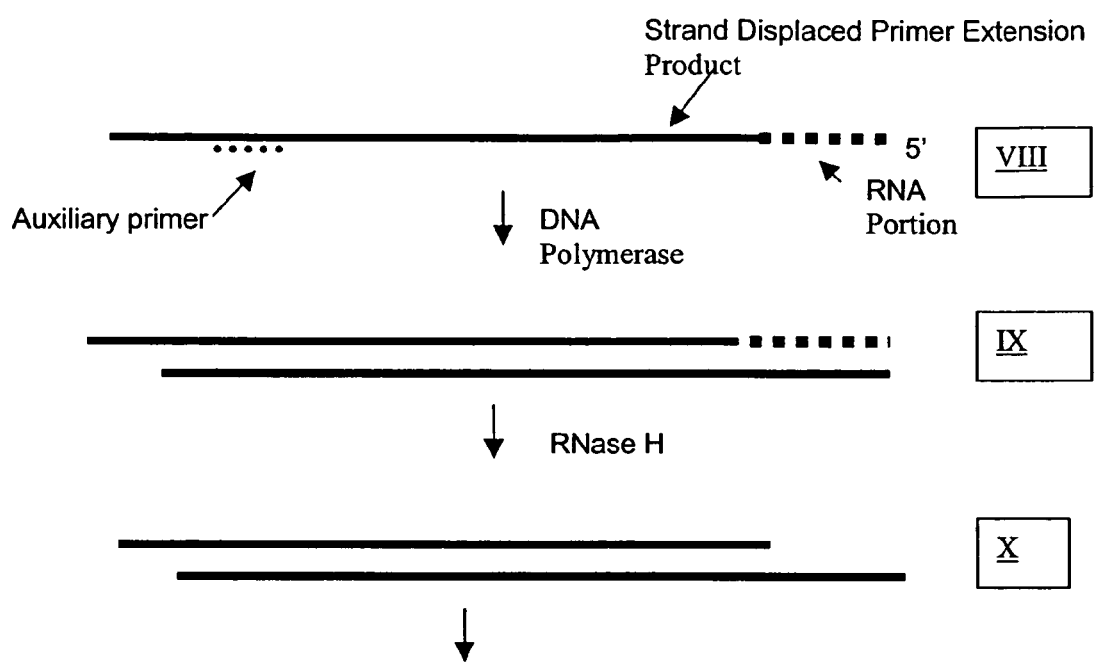
FIG. 8 illustrates generation of a second primer extension product primed by auxiliary primers hybridized to composite primer extension product.

Inclusion of auxiliary primers (i.e., a population of different random primers) during the amplification is believed to enhance the efficiency of production of and/or coverage of template polynucleotide. Without being bound by theory, it is believed that primer extension of auxiliary primers increases displacement of composite primer extension product from template polynucleotide and/or primes generation of second primer extension product. FIG. 7 illustrates primer extension from composite primers and auxiliary primers that are hybridized at multiple sites on a template strand. FIG. 8 illustrates generation of a second primer extension product primed by auxiliary primers hybridized to composite primer extension product.

Although for simplicity, use of auxiliary primers is described only in the first phase, random composite primer hybridization (i.e., step (a)), it is evident that auxiliary primers may be present in the reaction mixture for the second phase of the methods, single primer isothermal amplification (i.e., step (b)).

As is evident from the description and shown in the example, the methods of the invention are composite-primer dependent. That is, amplification is not observed in the absence of the composite primer.

Amplification Using a Composite Primer that Hybridizes to a Multiplicity of Template RNA Sites and Auxiliary Primers In another aspect of the invention, auxiliary primers are present in the reaction mixture comprising template RNA, composite primer, DNA-dependent DNA polymerase and RNA-dependent DNA polymerase. As used herein, "auxiliary primers" refers to a population of random or partially randomized primers. Inclusion of auxiliary primers (i.e., population of different random primers) during the amplification is believed to enhance the efficiency of production of and/or target coverage of the amplification product.

In some embodiments, the methods of the invention operate as follows: (a) incubating a reaction mixture, said reaction mixture comprising a composite primer as described herein; auxiliary primers; a template RNA, DNA-dependent DNA polymerase, and RNA-dependent DNA polymerase (which may be present as a single enzyme comprising both activities), wherein the incubation is under conditions suitable for random composite primer hybridization, auxiliary primer hybridization, primer extension, and strand displacement, whereby a complex comprising a RNA/DNA partial heteroduplex is generated; and (b) incubating a reaction mixture, said reaction mixture comprising the reaction products from step (a) (or an aliquot thereof); a composite primer (which may be the same as the composite primer of step (a) or may be a different composite primer); a DNA-dependent DNA polymerase; optionally, auxiliary primers; and an enzyme that cleaves RNA from an RNA/DNA hybrid; wherein the incubation is under conditions that permit primer hybridization, primer extension, RNA cleavage from an RNA/DNA heteroduplex, and displacement of the primer extension product from the complex when its RNA is cleaved and another composite primer binds to the template and is extended, whereby multiple copies of a polynucleotide template sequence are generated.

Inclusion of auxiliary primers (i.e., a population of different random primers) during the amplification is believed to enhance the efficiency of production of and/or coverage of template RNA. Without being bound by theory, it is believed that primer extension of auxiliary primers increases displacement of composite primer extension product from template RNA and/or primes generation of second primer extension product. FIG. 7 illustrates primer extension from composite primers and auxiliary primers that are hybridized at multiple sites on a template strand. FIG. 8 illustrates generation of a second primer extension product primed by auxiliary primers hybridized to composite primer extension product.

Although for simplicity, use of auxiliary primers is described only in the first phase, random composite primer hybridization (i.e., step (a)), it is evident that auxiliary primers may be present in the reaction mixture for the second phase of the methods, single primer isothermal amplification (i.e., step (b)).

As is evident from the description and shown in the example, the methods of the invention are composite-primer dependent. That is, amplification is not observed in the absence of the composite primer.

Components and Reaction Conditions Used in the Methods of the Invention

Template Nucleic Acid

The nucleic acid (NA) target to be amplified includes nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Preferred target polynucleotide includes DNA (e.g., genomic DNA, including human genomic DNA, and mammalian genomic DNA (such as mouse, rat,))and RNA (e.g., mRNA, ribosomal RNA, and total RNA). It should be understood that template RNA includes coding and non-coding RNA. The sequences can be naturally occurring or recombinant nucleic acid targets, including cloned nucleic fragments of interest.

The target nucleic acid can be only a minor fraction of a complex mixture such as a biological sample and can be obtained from various biological material by procedures well known in the art. Nucleic acid can be obtained from sources containing very small quantities of nucleic acid, such a single cells, small numbers of cells, patient samples, forensic samples, and archeological samples. Obtaining and purifying nucleic acids use standard techniques in the art, including methods designed to isolate one or a very small number of cells, such a cell sorting or laser capture micro-dissection. The methods of the invention are particularly suited for use with genomic DNA (e.g., human and other mammalian genomic DNA), as well as RNA (e.g., total RNA or mRNA samples). Amplification of an RNA target may be accomplished by initial cDNA synthesis, as known in the art, followed by amplification from the cDNA template.

The target polynucleotide(s) can be known or unknown and may contain more than one desired specific nucleic acid sequence of interest, each of which may be the same or different from each other. If the target polynucleotide is double stranded (e.g., double stranded DNA or a double stranded DNA/RNA hybrid, such as is produced by first strand cDNA synthesis), the target may first be treated to render it single stranded (e.g., by denaturation or by cleavage of the RNA portion of a DNA/RNA hybrid). Denaturation may also be carried out to remove secondary structure present in a single stranded target molecule (e.g., RNA). In some cases, double stranded DNA target polynucleotide may be first cleaved by one or more restriction endonuclease enzymes.

When the target polynucleotide is DNA, the initial step of the amplification of a target nucleic acid sequence is rendering the target single stranded. If the target nucleic acid is a double stranded (ds) DNA, the initial step can be target denaturation. The denaturation step may be thermal denaturation or any other method known in the art, such as alkali treatment. If the target nucleic acid is present in an DNA-RNA hybrid, the initial step can be denaturation of the hybrid to obtain a DNA, or removal of the RNA strand using other means known in the art, such as thermal treatment, digestion with an enzyme that cleaves RNA from an RNA/DNA hybrid (such as RNase H) or alkali treatment, to generate single stranded DNA. When the target is RNA, the initial step may be the synthesis of a single stranded cDNA. Techniques for the synthesis of cDNA from RNA are known in the art, and include reverse transcription of RNA strand using a primer that binds to a specific target, such as the poly-A tail of eukaryotic mRNAs or other specific or consensus sequences. In addition, reverse transcription can be primed by a population of degenerate or partially degenerate primers. First strand cDNA can be separated from the complex of RNA and first strand cDNA as described herein.

RNAs can be from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. It is understood that the RNA can be coding or noncoding RNA (such as untranslated small RNAs). RNAs can be obtained and purified using standard techniques in the art. Use of a DNA target (including genomic DNA target) would require initial transcription of the DNA target into RNA form, which can be achieved using methods disclosed in Kurn, U.S. Pat. No. 6,251,639 B1, and by other techniques (such as expression systems) known in the art. Thus, RNA template can be itself generated from a DNA source (such as genomic DNA), using methods known in the art, including Kurn, U.S. Pat. No. 6,251,639. RNA copies of genomic DNA would generally include untranscribed sequences generally not found in mRNA, such as introns, regulatory and control elements, etc. RNA targets may also be generated from cloned genomic DNA sequences that can be subjected to in vitro transcription. Use of a DNA-RNA hybrid would require denaturation of the hybrid to obtain a single stranded RNA, denaturation followed by transcription of the DNA strand to obtain an RNA, or other methods known in the art such as digestion with an RNAse H to generate single stranded DNA.

Composite Primer

The methods of the invention employ a composite primer that is composed of RNA and DNA portions. We have observed that suitable composite primers show partial nucleic acid sequence homology to a multiplicity of genomic DNA sequences, particularly in the 3' sequences of the composite primer, when analyzed using standard nucleic acid comparison algorithms. For example, composite primer sequence can be used as a query sequence in Blast, to search the human genomic DNA database (or other suitable database, such as a mammalian genomic DNA database). Generally, the search is performed using search parameters suitable for identification of partial or "low stringency" alignments, generally the least stringent conditions provided by the program. Such parameters are known in the art and include use of the NCBI Blast program for searching "short, nearly exact matches", with word size=7 (conditions permitting as few as 7 consecutive nucleotide perfect matches at any position in the primer sequence). See, e.g., http://www.ncbi.nlm.nih.gov/blast/Blast.cgi?ALIGNMENTS=50&ALIGNMENT_VIEW=Pairwise&AUTO_FORMAT=Semiauto&CLIENT=web&DATABASE=nr&DESCRIPTIONS=100&ENTREZ_QUERY=>(none)&EXPECT=1000&FORMAT_BLOCK_ON_RESPAGE=None&FORMAT_ENTREZ_QUERY=(none)&FORMAT_OBJECT=Alignment&FORMAT_TYPE=HTML&LAYOUT=TwoWindows&NCBI_GI=on&PAGE=Nucleotides&PROGRAM=blastn&SERVICE=plain&SET_DEFAULTS.x=16&SET_DEFAULTS.y=8&SHOW_OVER VIEW=on&WORD_SIZE=7&END_OF_HTTPGET=Yes. Composite primers useful in the methods of the invention (i.e., that randomly hybridize to template polynucleotide)

generally exhibit high partial homology rate with genomic DNA sequences, for example homology of stretches of 7 nucleotides with about 100 genomic DNA sequences, with about 70% of the hits located at the 3' end of the composite primer. A composite primer with a very unique sequence (i.e., low levels of homology with target genomic DNA sequences) did not function efficiently in the methods of the invention when used with genomic DNA template.

As is evident from the discussion above, reference to a primer that binds (hybridizes to) a sequence (or template) encompasses embodiments in which at least a portion of the primer is hybridized, embodiments in which two (or more portions) of the primer are hybridized (separated by unhybridized (looped out) portions of the primer), and embodiments in which the entire primer is hybridized. In certain embodiments, a 5'-portion, commonly the 5'-most portion, of the composite primer is designed such that the particular 5'-portion it is not expected to randomly hybridize to template polynucleotide (composite primers of this configuration are referred to as "tailed" primers, in reference to the 'tail' of unhybridized primer). In some embodiments, the tail portion of the composite primer is the entire 5' RNA portion of the composite primer. Thus, according to the methods of the invention, only a portion of the 3'-end of the composite primer must be hybridized in order for initiation of primer extension by DNA polymerase. In some embodiments, for example, only 2, 3, 4, 5, 6, 7 or more nucleotides of the 3' end of the primer must hybridize in order for primer extension to be initiated. It is understood that hybridization of the 3'-most portion of the composite primer may be stabilized to various extents by further hybridization of another portion of the primer (with or without looping out of intervening primer portions). A DNA polymerase can be included during primer hybridization to enhance (e.g., stabilize) hybridization of composite primer by initiation of primer extension, and thus, stabilization of primer hybridization.

We have also observed that composite primers that are suitable for use in the present methods can be identified by conducting single primer isothermal amplification as described in Kurn, U.S. Pat. No. 6,251,639, using the composite primer under high stringency conditions using a genomic DNA template, and observing the presence of a smear of reaction products as visualized, for example, on a gel. Preferably, the genomic DNA does not contain a sequence(s) that is complementary to the composite primer. Production of a "smear" of reaction products, i.e., generation of a complex mixture of product of multiple molecular weights, visible on a gel as a smear, indicates that the composite primer is randomly priming genomic DNA amplification.

In another example, single primer isothermal amplification of a specific synthetic target oligonucleotide (e.g., a target oligonucleotide comprising a specific target for composite primer hybridization) is conducted at high stringency in the presence or absence of genomic DNA template (e.g., 1-100 ng of human genomic DNA). Composite primers that are suitable for the methods of the invention will demonstrate a strong effect of genomic DNA on the efficiency of the amplification of the specific synthetic target, resulting in about a 100-fold or greater reduction of amplification efficiency as compared with amplification efficiency conducted in the absence of genomic DNA.

Random composite primer hybridization and/or generation of composite primer extension product is promoted by use of conditions designed to permit random (non-specific) primer hybridization. Such conditions are well known in the art, and are further discussed below, and include: decreased stringency during primer hybridization and/or first strand synthesis (including reduced temperature and/or buffer conditions of reduced stringency, such as reduced ionic strength); composite primer selection and/or design (discussed further herein); composite primer and template concentration, presence or absence of an agent that stabilizes a 3' hybridized primer (such as a DNA polymerase), and presence or absence of agents such as DMSO that lower the temperature requirements for stable hybridization. It is understood that the selection of reaction conditions may be used to control the frequency of composite primer hybridization, and thus control coverage and/or representation of template polynucleotide sequences in amplification product.

Generally, the composite primer is also designed so that there is no primer-dimer formation capability, as determined using software routinely available to one of ordinary skill in the art, e.g. Oligo Primer Analysis Software from Molecular Biology Insight, and references therein. One of skill in the art will understand that other factors affect nucleic acid hybridization affinities. For example, any and all of the guanosine-cytosine content of the primer-target and primer-primer duplexes, minor groove binders, O-methylation or other modification of nucleotides, temperature, and salt are potentially important factors in constructing primers with the requisite differences in binding energies. Another factor in designing and constructing primers is the free energy parameters of hybridization of given sequences under a given set of hybridization conditions. The free energy parameters for the formation of a given hybrid may be calculated by methods known in the art (see, e.g., Tinoco et al. *Nature* (1973) 246: 40-41 and Freier et al., *Proc. Natl. Acad. Sci. USA* (1986) 83:9373-9377; computer programs, e.g., Oligo Primer Analysis Software from Molecular Biology Insight, and references therein), and it is possible to predict, for a given oligonucleotide template, primer sequences for which the required free energy changes for formation of various complexes will be met.

The primers should be extendable by DNA polymerase. Generation of primers suitable for extension by polymerization is well known in the art, such as described in PCT Pub. No. WO99/42618 (and references cited therein). Generally, the primer should permit high efficiency of amplification of a synthetic target that contains a specific primer target binding site (e.g., the complementary sequence to the primer), for example, permitting amplification of about $10^6$ to $10^9$ using methods described in Kurn, U.S. Pat. No. 6,251,639. The composite primer is designed such that subsequent displacement of the primer extension product by binding of a new (additional) composite primer and the extension of the new primer by the polymerase can be achieved. In addition, cleavage of the RNA portion of the primer extension product leads to generation of amplification product which is not a substrate for amplification by the composite primer. It is understood that, in the following section that generally describes aspects of the composite primers used in the methods of the invention, characteristics described may be applicable to the primers if used for hybridizing and initiating the polynucleotide amplification (production of composite extension product) and/or for single primer isothermal amplification as described herein.

In some embodiments, a first composite primer is used in the methods of the invention, including those steps which involve single primer isothermal amplification (i.e., phase (b)). In other embodiments, a first and second, different, composite primer are used in the methods of the invention. The second composite primer is used for the single primer isothermal amplification step, and may comprise some or all of the sequence of the first composite primer, and the first composite primer may comprise some or all of the sequence of the second composite primer. In some embodiments, the second composite primer comprises a different sequence than the first composite primer.

For use in single primer isothermal amplification and/or composite primer extension product formation, a composite primer comprises at least one RNA portion that is capable of (a) binding (hybridizing) to a sequence on the single stranded portion of the complex (formed by cleavage of RNA in the complex comprising a RNA/DNA partial heteroduplex) (in some embodiments, on second primer extension product) independent of hybridization of the DNA portion(s) to a sequence on the same single stranded portion; and (b) being cleaved with an agent such as a ribonuclease when hybridized to the single stranded portion. The composite primers bind to the single stranded portion, and are extended by DNA polymerase to form a RNA/DNA partial heteroduplex in which only the RNA portion of the primer is cleaved upon contact with an agent which cleaves RNA in an RNA/DNA hybrid, such as an enzyme, such as a ribonuclease (such as RNase H), while the composite primer extension product remains intact, thus enabling annealing of another composite primer.

When used for the single primer isothermal amplification described herein, the composite primers also comprise a 3' DNA portion that is capable of hybridization to a sequence on the 3' single stranded portion of the complex such that its hybridization to the 3' single stranded portion is favored over that of the nucleic acid strand that is displaced from the complex by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the complex (e.g., in the second primer extension product) favored over the hybridization of the homologous sequence in the 5' end of the displaced strand to the composite primer extension product.

The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 50, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 14, 15, 20, 25, 3, 50 nucleotides. In certain embodiments, the composite primer has an RNA portion of about 14 or about 20 nucleotides.

The length of the 5'-RNA portion in a composite primer comprising a 5'-RNA portion and a 3'-DNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 14, 15, 17, 18, 20, 50 nucleotides. In certain embodiments, the composite primer has an RNA portion of about 14 or about 20 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 14, 15, 17, 18, 20, 50 nucleotides. In certain embodiments, the composite primer has an RNA portion of about 14 or about 20 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides.

The length of the 3'-DNA portion in a composite primer comprising a 5'-RNA portion and a 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. In one embodiment, the composite primer has a 3'-DNA portion of about 7 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 50 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 50, 60 nucleotides. In certain embodiments, the composite primer is about 21 or about 27 nucleotides in length. It is understood that the length can be greater or less, as appropriate under the reaction conditions of the methods of this invention.

As described herein, one or more different composite primers may be used in an amplification reaction.

Auxiliary Primers

"Auxiliary primer" as used herein, are a population of primers comprising randomized and/or partially-randomized sequences. Auxiliary primers are a polynucleotide as described herein, though generally, auxiliary primers are made of DNA. Such random primers are known in the art. An example of auxiliary primers is the population of randomized hexamer primers shown in Example 1. In some embodiments, the random primers may contain natural or non-natural nucleotide(s) that permit non-specific hybridization in order to increase the number of sequences to which the random primers may bind. Similarly, abasic sites can be introduced randomly within the population of random primers, which can permit non-specific hybridization by stabilizing mismatches between primer and template. The primers should be extendable by DNA polymerase. Generation of primers suitable for extension by polymerization is well known in the art, such as described in PCT Pub. No. WO 99/42618 (and references cited therein).

In some embodiments, auxiliary primers can be at least 6, at least 7, at least 8, at least 9, at least 10, at least 11, at least 12, at least 15, at least 18, at least 20, or more nucleotides in length. In some embodiments, a population of primers of differing lengths is used.

DNA Polymerase, and an Agent Capable of Cleaving an RNA-DNA Hybrid

The amplification methods of the invention employ the following enzymes: an RNA-dependent DNA polymerase, a DNA-dependent DNA polymerase, and an agent capable of cleaving an RNA strand of an RNA-DNA hybrid (for example, a ribonuclease such as RNase H). One or more of these activities may be found and used in a single enzyme. For example, RNase H activity may be supplied by an RNA-dependent DNA polymerase (such as reverse transcriptase) or may be provided in a separate enzyme. Reverse transcriptases useful for this method may or may not have RNase H activity. Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks the RNase H activity. Reverse transcriptase devoid of RNase H activity are known in the art, including those comprising a mutation of the wild type reverse transcriptase where the mutation eliminates the RNase H activity. In these cases, the addition of an RNase H from other sources, such as that isolated from $E.\ coli$, can be employed for the formation of the double stranded cDNA. The RNA-dependent DNA polymerase activity and DNA-dependent DNA polymerase activity may be provided by the same enzyme (for example, Bst polymerase), or these activities may be provided in separate enzymes.

One aspect of the invention is the formation of a complex comprising an RNA/DNA partial heteroduplex. This process generally utilizes the enzymatic activities of an RNA-dependent DNA polymerase, a DNA-dependent DNA polymerase. Generally, RNA in the RNA/DNA partial heteroduplex is cleaved by an agent (such as an enzyme, such as a ribonuclease) capable of cleaving RNA from an RNA/DNA hybrid, generating a 3' single stranded portion with sequences that are complementary to RNA in a composite primer (and thus forming a binding site for a composite primer).

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase and, for example, a DNA polymerase that possesses both DNA-dependent and RNA-dependent DNA polymerase activity, such as Bst DNA polymerase.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxynucleotides. The formation of the complex comprising the RNA/DNA partial heteroduplex can be carried out by a DNA polymerase which comprises both RNA-dependent DNA polymerase and DNA-dependent DNA polymerase activities (such as Bst DNA polymerase, or a reverse transcriptase). Amplification of an RNA sequence according to methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the DNA polymerase preferably has little or no 5'->3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'->3' exonuclease activity has been deleted, are known in the art and are suitable for the amplification methods described herein. Mutant DNA polymerases which lack both 5' to 3' nuclease and 3' to 5' nuclease activities have also been described, for example, exo$^{-/-}$Klenow DNA polymerase. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Preferably, the DNA polymerase has little to no proofreading activity Suitable DNA polymerases for use in the methods and compositions of the invention include those disclosed in U.S. Pat. Nos. 5,648,211 and 5,744,312, which include exo$^-$ Vent (New England Biolabs), exo$^-$ Deep Vent (New England Biolabs), Bst (BioRad), exo$^-$ Pfu (Stratagene), Bca (Panvera), sequencing grade Taq (Promega), exo$^{-/-}$Klenow DNA polymerase, and thermostable DNA polymerases from thermoanaerobacter thermohydrosulfuricus.

The ribonuclease for use in the methods and compositions of the invention is capable of cleaving ribonucleotides in an RNA/DNA hybrid. Preferably, the ribonuclease cleaves ribonucleotides in an RNA/DNA hybrid regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H (RNase H), e.g., Hybridase.

As is well known in the art, DNA-dependent DNA polymerase activity, RNA-dependent DNA polymerase activity, and the ability to cleave RNA from a RNA/DNA hybrid may be present in different enzymes, or two or more activities may be present in the same enzyme. Accordingly, in some embodiments, the same enzyme comprises RNA-dependent DNA polymerase activity and cleaves RNA from an RNA/DNA hybrid. In some embodiments, the same enzyme comprises DNA-dependent DNA polymerase activity and cleaves RNA from an RNA/DNA hybrid. In some embodiments, the same enzyme comprises DNA-dependent DNA polymerase activity, RNA-dependent DNA polymerase activity and cleaves RNA from an RNA/DNA hybrid. In some embodiments, different enzymes comprise RNA-dependent DNA polymerase activity and DNA-dependent DNA polymerase activity. In some embodiments, different enzymes comprise RNA-dependent DNA polymerase activity and cleave RNA from an RNA/DNA hybrid. In some embodiments, different enzymes comprise DNA-dependent DNA polymerase activity and cleave RNA from an RNA/DNA hybrid.

In general, the enzymes used in the methods and compositions of the invention should not produce substantial degradation of the nucleic acid components of said methods and compositions.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA or acetylated BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. Preferably, the amplification reactions (particularly, primer extension other than the composite and second primer extension product synthesis steps, and strand displacement) are performed isothermally, which avoids the cumbersome thermocycling process. The amplification reaction is carried out at a temperature that permits hybridization of the oligonucleotides (primer) of the invention to the template polynucleotide and primer extension products, and that does not substantially inhibit the activity of the enzymes employed. The temperature can be in the range of 0° C. to about 85° C., about 25° C. to about 85° C., about 30° C. to about 80° C., and about 37° C. to about 75° C.

Random priming and/or primer extension and/or isothermal amplification can be conducted under conditions of reduced stringency (i.e., permitting hybridization of sequences that are not fully complementary). For a given set of reaction conditions, the ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Conversely, the lower the stringency of the conditions for hybridization, the lower the complementarity necessary for binding between the hybridizing and/or partially hybridizing composite primer and template polynucleotide. Decreased stringency is achieved by any one or more of the following: reducing the temperature, decreasing the ratio of cosolvents, lowering the salt concentration, and the like. Conditions that increase or reduce the stringency of a hybridization reaction are widely known and published in the art. See, for example, Sambrook et al. (1989), and in Ausubel (1987), supra. Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press San Diego, Calif. The hybridization conditions chosen depend on a variety of factors known in the art, for example the length and type (e.g., RNA, DNA, PNA) of primer and primer binding region of the oligonucleotide template, as well as the concentration of primer and template polynucleotides.

Insofar as it is convenient to use buffer conditions that are compatible with DNA polymerase activity and/or ribonuclease activity, stringency of hybridization of composite primers can be controlled by altering temperature of the reaction. Examples of relevant conditions include (in order of increasing stringency): incubation temperatures of approximately 15° C., 20° C., 25° C., 30° C., 37° C., 40° C., 45° C., 50° C., 60° C., or more. Accordingly, in some embodiments, composite primer random hybridization occurs at a reduced temperature, for example at 25° C.-37° C., followed at incubation at increased temperature(s) suitable for the isothermal amplification phase of the methods (such as about 50° C.). In some embodiments, temperature is increased at 5° C. increments. In other embodiments, temperature is shifted from low to high temperature.

Nucleotide and/or nucleotide analogs, such as deoxyribonucleoside triphosphates, that can be employed for synthesis of the primer extension products in the methods of the invention are provided in the amount of from preferably about 50 to about 2500 μM, more preferably about 100 to about 2000 μM, even more preferably about 200 to about 1700 μM, and most preferably about 250 to about 1500 μM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Composite primers can each be provided at about or at least about any of the following concentrations: 50 nM, 100 nM, 500 nM, 1 uM, 2.5 uM, 5 uM, 10 uM. Composite primer concentration also impacts frequency and/or position of composite primer hybridization. Generally, increased primer concentrations increased frequency of primer hybridization. Auxiliary primers can be provided at about or at least about any of the following concentrations: about 25 nM, about 50 nM, about 100 nM, about 500 nM, about 1 uM, about 2.5 uM, about 5 uM, about 10 uM, or more.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target polynucleotide, as determined by their thermal stability and/or other considerations known to the person of skill in the art. In these embodiments, the reaction conditions and components may be varied between the different reactions.

The amplification process can be stopped at various timepoints, and resumed at a later time. Said timepoints can be readily identified by a person of skill in the art. One timepoint is at the end of random composite primer hybridization. Another timepoint is at the end of random composite primer hybridization and composite primer extension product synthesis. Another timepoint (in some embodiments) is following cleavage of template RNA. Another timepoint is immediately prior to initiation of single primer isothermal amplification (which in some embodiments, may be initiated by addition of an enzyme (such as RNase H) that cleaves RNA from RNA/DNA heteroduplex, and optionally, DNA polymerase). Another timepoint is at the end of second primer extension product synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity, replenishing a destroyed (depleted) enzyme, or adding reagent(s) necessary for initiation of a step (for example, addition of RNase H and/or DNA polymerase to initiate the single primer isothermal amplification phase of the methods). In some embodiments, one or more of the components of the reactions is replenished prior to, at, or following the resumption of the reactions. For example, it may be necessary to replenish the composite primer prior to beginning the single primer isothermal amplification reaction if the same composite primer is being used. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art. One timepoint is at the end of formation of the complex comprising an RNA/DNA partial heteroduplex. Another timepoint is at the end of random composite primer hybridization.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined.

Compositions and Kits of the Invention

The invention also provides compositions and kits used in the methods described herein. The compositions may be any component(s), reaction mixture and/or intermediate described herein, as well as any combination.

In one embodiment, the invention provides a composition comprising a composite primer as described herein. In some embodiments, the composite primer comprises an RNA portion adjacent to the DNA portion. In another embodiment, the composite primer comprises 5'- and 3'-DNA portions with at least one intervening RNA portion. In other embodiments, the RNA portion of the composite primer consists of 7 to about 20 nucleotides and the DNA portion of the composite primer consists of about 5 to about 20 nucleotides. In still other embodiments, the RNA portion of the composite primer consists of about 10 to about 20 nucleotides and the DNA portion of the composite primer consists of about 7 to about 20 nucleotides. In some embodiments, the composite primer is selected from the following composite primers: 5'-GACG-GAUGCGGUCUdCdCdAdGdTdGdT-3' (SEQ ID NO:1); and 5'-CGUAUUCUGACGACGUACUCdTd-CdAdGdCdCdT-3' (SEQ ID NO:2), wherein italics denote ribonucleotides and "d" denotes deoxyribonucleotides.

In other examples, the invention provides a composition comprising a composite primer as described herein, and auxiliary primers (for example, a population of randomized hexamer primers). In some embodiments, the composite primer is selected from the following composite primers: 5'-GACG-GAUGCGGUCUdCdCdAdGdTdGdT-3' (SEQ ID NO:1); and 5'-CGUAUUCUGACGACGUACUCdTd-CdAdGdCdCdT-3' (SEQ ID NO:2), wherein italics denote ribonucleotides and "d" denotes deoxyribonucleotides.

In other examples, the invention provides a composition comprising a composite primer that is derivatized by attachment of a moiety capable of effecting attachment of a polynucleotide comprising the composite primer to a solid substrate used in preparing nucleic acid microarrays. In some embodiments, the composite primer is further by attachment of a positively charged moiety such as an amine. In other embodiments, the composite primer is labeled, for example by derivatizing the composite primer with a detectable moiety, such as a label, or a moiety that can be covalently or non-covalently attached to a label. Labeled composite primers are further described herein.

In other examples, the invention provides composition comprising a composite primer and one or more of: a DNA polymerase; an enzyme that cleaves RNA from an RNA/DNA duplex; and auxiliary primers (for example, a population of random hexamer primers). In some embodiments, the composition further comprises a labeled dNTP. In still other embodiments, the composition comprises a non-canonical nucleotide (such as dUTP), and reagents suitable for labeling and/or fragmenting abasic sites, as described in U.S. Patent Application Publication No. 2004/0005614 and Kurn et al, co-pending U.S. patent application No. 60/533,381.

The compositions are generally in lyophilized or aqueous form, preferably in a suitable buffer.

The invention also provides compositions comprising the amplification products described herein. Accordingly, the invention provides a population of DNA which are copies or the complement of a target sequence, which are produced by any of the methods described herein (or compositions comprising the products). The invention also includes compositions and various configurations (such as arrays) of these populations, which may be homogeneous (same sequence) or heterogeneous (different sequence). These populations may be any assembly of sequences obtained from the methods described herein.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: methods of amplification; genotyping, nucleic acid mutation detection (including methods of genotyping), determining the presence or absence of a sequence of interest, quantitating a sequence of interest, preparation of an immobilized nucleic acid (which can be a nucleic acid immobilized on a microarray), comparative genomic hybridization, and characterizing nucleic acids using the amplified nucleic acid products generated by the methods of the invention, methods of expression profiling, subtractive hybridization and the preparation of probes for subtractive hybridization, and methods of preparing libraries (which may be cDNA and/or differential hybridization libraries).

The kits of the invention comprise one or more containers comprising any combination of the components described herein, and the following are examples of such kits. A kit may comprise any of the composite primers described herein. In some embodiments, the kit comprises one or more composite primer selected from the following composite primers: 5'-GACGGAUGCGGUCUdCdCdAdGdTdGdT-3 (SEQ ID NO:1); and 5'-CGUAUUCUGACGACGUACUCdTd-CdAdGdCdCdT-3' (SEQ ID NO:2), wherein italics denote ribonucleotides and "d" denotes deoxyribonucleotides. In some embodiments, a kit further comprises auxiliary primers, which may or may not be separately packaged. The composite primer may be labeled or unlabeled. Kits may also optionally further include any of one or more of the enzymes described herein (for example, DNA-dependent DNA polymerase, RNA-dependent DNA polymerase, a DNA polymerase that provides both DNA-dependent and RNA-dependent DNA polymerase activities, and an enzyme capable of cleaving RNA from an RNA/DNA hybrid, such as RNase H), as well as deoxynucleoside triphosphates (labeled or unlabeled or derivatized). Kits may also include one or more suitable buffers (for example, as described herein). Kits may also include a labeled dNTP(s) and/or a non-canonical nucleotide (such as dUTP), as described in Kurn et al, co-pending U.S. patent application No. 60/381,457.

One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the invention for the intended nucleic acid amplification, and/or, as appropriate, for using the amplification products for purposes such as detection of sequence mutation. The instructions included with the kit generally include information as to reagents (whether included or not in the kit) necessary for practicing the methods of the invention, instructions on how to use the kit, and/or appropriate reaction conditions.

In another example, the kits of the invention comprise a complex of composite primer extension product and second primer extension product. In yet another example, any of these kits further comprises one or more controls (which can be, for example, template polynucleotide (e.g., DNA template such as genomic DNA or RNA template such as total RNA or mRNA), composite primers, and/or auxiliary primer(s).

The component(s) of the kit may be packaged in any convenient, appropriate packaging. The components may be packaged separately, or in one or multiple combinations.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise various combinations of the components discussed above.

Any of the systems embodiments may also comprise a template (target) sequence, as described herein. A system generally includes one or more apparatuses for performing the amplification methods of the invention. Such apparatuses include, for example, heating devices (such as heating blocks or water baths) and apparatuses which effect automation of one or more steps of the methods described herein. The methods of the invention are particularly suitable for use with miniaturized devices, as thermal cycling is not required for any of the steps. A non-limiting example of suitable devices includes the BioAnalyzer (Agilant and Caliper) and the eSensor.

The invention also provides reaction mixtures (or compositions comprising reaction mixtures) which contain various combinations of components described herein. Examples of reaction mixtures have been described. In some embodiments, the invention provides reaction mixtures comprising (a) a target polynucleotide; (b) a composite primer comprising a 3' DNA portion and an RNA portion; (c) auxiliary primers; and (d) DNA polymerase. As described herein, any of the composite primers may be in the reaction mixture (or a plurality of composite primers), including a composite primer that comprises a 5' RNA portion which is adjacent to the 3' DNA portion. The reaction mixture could also further comprise an enzyme which cleaves RNA from an RNA/DNA hybrid, such as RNase H. In some embodiments, the composite primer is selected from the following composite primers: 5'-GACGGAUGCGGUCUdCdCdAdGdTdGdT-3 (SEQ ID NO:1); and 5'-CGUAUUCUGACGACGUACUCdTd-CdAdGdCdCdT-3' (SEQ ID NO:2), wherein italics denote ribonucleotides and "d" denotes deoxyribonucleotides.

Other reaction mixtures are described herein and are encompassed by the invention.

The invention also includes compositions comprising any of the complexes (which are intermediates in the methods described herein) described herein. Examples of such complexes are schematically depicted in FIGS. 1-8. As an example, one complex of the invention is a complex comprising: (a) a target polynucleotide strand; and (b) a composite primer, said composite primer comprising a 3' DNA portion and an RNA portion. The composite primer may have an RNA portion which is 5' and adjacent to the 3" DNA portion. As another example, a complex of the invention is a complex comprising: (a) a composite primer extension product; and (b) a target polynucleotide.

In yet another example, a complex of the invention is a complex comprising a RNA/DNA partial heteroduplex, prepared by any of the methods described herein. In some embodiments, the complex further comprises a second RNA/DNA partial heteroduplex at a second end. In yet another example, the complex of the invention is a complex comprising a 3' single stranded DNA portion produced by any of the methods described herein. In some embodiments, the complex further comprises a second 3' single stranded region. In another example, the complex of the invention is (a) a complex comprising a 3' single stranded DNA portion, and (b) a composite primer hybridized to the 3' single stranded portion.

Methods Using the Amplification Methods and Compositions of the Invention

The methods and compositions of the invention can be used for a variety of purposes. For purposes of illustration, methods of nucleic acid mutation detection (including methods of genotyping), determining the presence or absence of a sequence of interest, quantitating a sequence of interest, preparation of an immobilized nucleic acid (which can be a nucleic acid immobilized on a microarray), comparative genomic hybridization, and characterizing nucleic acids using the amplified nucleic acid products generated by the methods of the invention, detecting and/or identifying novel nucleic acid sequences (such as novel coding or non-coding transcripts), and characterization of splice variant sequences, are described. Methods of expression profiling, methods of subtractive hybridization and the preparation of probes for subtractive hybridization, and methods of preparing libraries (which can be cDNA and/or differential hybridization libraries) are also described.

Method of Preparing Nucleic Acids Immoblized to a Substrate, Including a Microarray of Nucleic Acids The products of some of the amplification methods of the invention are suitable for immobilizing to a surface. In so far as the amplification products of the methods of the invention generally comprises a mixture of sequences corresponding to sense and antisense copies of template polynucleotide, it is useful to immobilize a population of sequences generated by amplification of template polynucleotide from a defined source (e.g., DNA or RNA from a defined cell population or a single cell; organism-specific template (for example, the DNA or RNA of specific viruses or other pathogen(s) sufficient to identify the organism); or a disease-specific template. Immobilized amplification product may then be probed with different probes and the hybridization signals can be compared. For example, an immobilized array of genomic polynucleotides (DNA or RNA) from a known pathogen or non-pathogen(such as a virus, or group of viruses) may be used for assessment of the presence or identity of a pathogen within a sample of genetic material. Such arrays would be of use in disease surveillance and in identification of a pathogenic agent in the event of a disease outbreak. Polynucleotides may be isolated from a suspected sample, labeled using any method known in the art, and hybridized to such an array. The detection of signal due to hybridization to the array provides information as to the presence or identity of a pathogen present in sample polynucleotide.

Amplification products can be attached to a solid or semi-solid support or surface, which may be made, e.g., from glass, plastic (e.g., polystyrene, polypropylene, nylon), polyacrylamide, nitrocellulose, or other materials.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplification product is then contacted with a solid substrate, such as a glass slide, which is coated with an aldehyde or another reactive group which will form a covalent link with the reactive group that is on the amplification product and become covalently attached to the glass slide. Microarrays comprising the amplification products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., *Proc. Natl. Acad. Sci. U.S.A.* (1995) 93:10614-10619). Arrays can also be printed by robotics onto glass, nylon (Ramsay, G., *Nature Biotechnol.* (1998), 16:40-44), polypropylene (Matson, et al., *Anal Biochem.* (1995), 224(1):110-6), and silicone slides (Marshall, A. and Hodgson, J., *Nature Biotechnol.* (1998), 16:27-31). Other approaches to array assembly include fine micropipetting within electric fields (Marshall and Hodgson, supra), and spotting the polynucleotides directly onto positively coated plates. Methods such as those using amino propyl silicon surface chemistry are also known in the art, as disclosed at http://www.cmt.corning.com and http://cmgm.stanford.edu/pbrown/.

One method for making microarrays is by making high-density polynucleotide arrays. Techniques are known for rapid deposition of polynucleotides (Blanchard et al., Biosensors & *Bioelectronics,* 11:687-690). Other methods for making microarrays, e.g., by masking (Maskos and Southern, *Nuc. Acids. Res.* (1992), 20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

The amplified polynucleotides may be spotted as a matrix on substrates comprising paper, glass, plastic, polystyrene, polypropylene, nylon, polyacrylamide, nitrocellulose, silicon, optical fiber or any other suitable solid or semi-solid (e.g., thin layer of polyacrylamide gel (Khrapko, et al., *DNA Sequence* (1991), 1:375-388) surface.

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization and detection of target molecules. In one embodiment the substrate to which the amplification products are attached is magnetic beads or particles. In another embodiment, the solid substrate comprises an optical fiber. In yet another embodiment, the amplification products are dispersed in fluid phase within a capillary which, in turn, is immobilized with respect to a solid phase.

Arrays may also be composed of particles, such as beads. The beads may be labeled with the amplified products alone, or may be labeled with both the amplified products and an additional label, such as defined dyes or other labels.

Characterization of Nucleic Acids

The amplification products obtained by the methods of the invention are amenable to further characterization. The products of the methods of the invention are particularly amenable to quantitative analysis, as sufficient DNA is produced which generally accurately reflect the representation of the various polynucleotides in the starting material.

The amplified polynucleotide products (i.e., products of any of the amplification methods described herein), can be analyzed using, for example, probe hybridization techniques known in the art, such as Southern and Northern blotting, and hybridizing to probe arrays. They can also be analyzed by electrophoresis-based methods, such as differential display and size characterization, which are known in the art. In addition, the polynucleotide products may serve as starting material for other analytical and/or quantification methods known in the art, such as real time PCR, quantitative TaqMan, quantitative PCR using molecular beacons, methods described in U.S. Pat. Nos. 6,251,639, 6,686,156, and 6,692,918; U.S. Patent Publication Nos. 2002/0115088 A1, 2003/0186234 A1, 2003/0087251A1, 2002/0164628, and 2003/0215926, and International Patent Application Publication WO 03/08343. Thus, the invention includes those further analytical and/or quantification methods as applied to any of the products of the methods herein.

In one embodiment, the amplification methods of the invention are utilized to generate multiple copies of polynucleotide products, and products are analyzed by contact with a probe.

In some embodiments, the amplification methods of the invention are utilized to generate multiple copies of single stranded polynucleotide (generally, DNA) products that are labeled by using composite primers that are labeled (in the portion(s) that is not cleaved). For example, the primer can be labeled with an aminoallyl labeled nucleotide. In other embodiments, the amplification methods of the invention are utilized to generate multiple copies of polynucleotide (generally, DNA) products that are labeled by the incorporation of labeled nucleotides during DNA. For example, amplification according to the methods of the invention can be carried out with suitable labeled dNTPs. These labeled nucleotides can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of template polynucleotide according to the methods of the invention in the presence of, for example, Cy3-dUTP or Cy5-dUTP results in the incorporation of these nucleotides into the amplification products. Amplification can also be in the presence of an aminoallyl-derivatized nucleotide, such as aminoallyl dUTP. Amplification product comprising aminoallyl dUTP can be coupled to a label, such as Cy3 or Cy5.

In other embodiments, the methods of the amplification are performed in he present of a non-canonical nucleotide, e.g., dUTP, and amplification comprising a non-canonical nucleotide is labeled and/or fragmented according to the methods disclosed in U.S. Patent Application Publication No. 2004/0005614. Briefly, non-canonical nucleotide (when incorporated into amplification product) is cleaved, generating an abasic site. The abasic site is then labeled by contacting with a reagent capable of labeling an abasic site. The polynucleotide comprising an abasic site can also be cleaved at the abasic site, generating fragments suitable for further analysis, e.g., hybridization to an array. The fragments can also be labeled as described above.

The labeled amplification products are particularly suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) an target polynucleotide of interest by generating labeled polynucleotide (generally, DNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays, which have been described above. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplification products, and thus by extrapolation the identity of the target polynucleotide present in a sample. Hybridization of the labeled products is detectable, and the amount of specific labels that are detected is proportional to the amount of the labeled amplification products of a specific target polynucleotide of interest.

The amount of labeled products (as indicated by, for example, detectable signal associated with the label) hybridized at defined locations on an array can be indicative of the detection and/or quantification of the corresponding target polynucleotide species in the sample.

Methods of characterization include sequencing by hybridization (see, e.g., Dramanac, U.S. Pat. No. 6,270,961) and global genomic hybridization (also termed comparative genome hybridization) (see, e.g., Pinkel, U.S. Pat. No. 6,159,685; Daigo et al (2001) Am. J. Pathol. 158 (5):1623-1631. Briefly, comparative genome hybridization comprises preparing a first population of labeled polynucleotides (which can be polynucleotide fragments) according to any of the methods described herein, wherein the template from which the first population is synthesized is total genomic DNA. A second population of labeled polynucleotides (to which the first population is desired to be compared) is prepared from a second genomic DNA template. The first and second populations are labeled with different labels. The hybridized first and second populations are mixed, and hybridized to an array or chromosomal spread. The different labels are detected and compared.

In another aspect, the invention provides a method of quantitating labeled and/or fragmented nucleic acids comprising use of an oligonucleotide (probe) of defined sequence (which may be immobilized, for example, on a microarray).

The amplification products generated according to the methods of the invention are also suitable for analysis for the detection of any alteration in the target nucleic acid sequence, as compared to a reference nucleic acid sequence which is identical to the target nucleic acid sequence other than the sequence alteration. When the target polynucleotide is genomic DNA or RNA, the sequence alterations may be sequence alterations present in the genomic sequence or may be sequence alterations which are not reflected in the genomic sequence, for example, alterations due to post transcriptional alterations, and/or mRNA processing, including splice variants. Sequence alterations (interchangeably called "mutations") include deletion, substitution, insertion and/or transversion of one or more nucleotide.

Other art recognized methods of analysis for the detection of any alteration in the target nucleic acid sequence, as compared to a reference nucleic acid sequence, are suitable for use with the nucleic acid products of the amplification methods of the invention. Such methods are well-known in the art, and include various methods for the detection of specific defined sequences including methods based on allele specific primer extension, allele specific probe ligation, differential probe hybridization, and limited primer extension. See, for example, Kurn et al, U.S. Pat. No. 6,251,639 B1; U.S. Pat. Nos. 5,888,819; 6,004,744; 5,882,867; 5,854,033; 5,710,028; 6,027,889; 6,004,745; 5,763,178; 5,011,769; 5,185,243; 4,876,187; 5,882,867; 5,731,146; WO US88/02746; WO 99/55912; WO 92/15712; WO 00/09745; WO 97/32040; WO 00/56925; and U.S. Pat. No. 5,660,988. Thus, the invention also provides methods for detection of a mutation in a target polynucleotide comprising a mutation (which can be a single nucleotide polymorphism), comprising: (a) amplifying a target polynucleotide using any of the methods described herein; and (b) analyzing the amplification products for presence of an alteration (mutation) as compared to a reference polynucleotide.

It is understood that the amplification products can also serve as template for further analysis such as sequence, polymorphism detection (including multiplex SNP detection) using, e.g., oligonucleotide ligation-based assays, analysis using Invader, Cleavase or limited primer extension, and the like. For methods that generally require larger volumes of input material, the methods of the invention may be used to "pre" amplify a pool of polynucleotides to generate sufficient input material for subsequent analysis.

Determination of Gene Expression Profile

The amplification methods of the invention are particularly suitable for use in determining the levels of expression of one or more genes in a sample since the methods described herein are capable of amplifying a multiplicity, including a large multiplicity of target RNAs in the same sample. As described above, amplification products can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of RNA sequences of interest present in a sample, as determined by quantifying amplification products of the sequences, provides for determination of the gene expression profile of the sample source.

Accordingly, the invention provides methods of determining gene expression profile in a sample, said method comprising: amplifying single stranded product from template RNA s in the sample, using any of the methods described herein; and determining amount of amplification products of each RNA, wherein each said amount is indicative of amount of each RNA in the sample, whereby the expression profile in the sample is determined. Generally, labeled products are generated. In certain embodiments, the target RNA is mRNA. It is understood that amount of amplification product may be determined using quantitative and/or qualitative methods. Determining amount of amplification product includes determining whether amplification product is present or absent. Thus, an expression profile can includes information about presence or absence of one or more RNA sequence of interest. "Absent" or "absence" of product, and "lack of detection of product" as used herein includes insignificant, or de minimus levels.

The methods of expression profiling are useful in a wide variety of molecular diagnostic, and especially in the study of gene expression in essentially any mammalian cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Method of Preparing a Library

The DNA products of the methods of the invention are useful in preparing libraries, including cDNA libraries and subtractive hybridization libraries. Using the methods of the invention, libraries may be prepared from limited amount of starting material, for example, mRNA extracted from limited amount of tissue or even single cells. Accordingly, in one aspect, the methods of the invention provides preparing a library from the DNA products of the invention. In still another aspect, the invention provides methods for making a library, said method comprising: preparing a subtractive hybridization probe using any of the methods described herein.

Methods of Subtractive Hybridization

The amplification methods of the invention are particularly suitable for use in subtractive hybridization methods, in which (at least) a first and second target polynucleotide population is compared, since the methods described herein are capable of amplifying multiple target polynucleotides in the same sample, and the methods of the invention are suitable for producing large amounts of single stranded antisense nucleic acid suitable for use as "driver" in subtractive hybridization. For example, two nucleic acid populations, one sense and one antisense, can be allowed to mix together with one population present in molar excess ("driver"). Sequence present in both populations will form hybrids, while sequences present in only one population remain single-stranded. Thereafter, various well known techniques are used to separate the unhybridized molecules representing differentially expressed sequences. See, e.g., Hamson et al., U.S. Pat. No. 5,589,339; Van Gelder, U.S. Pat. No. 6,291,170. The methods of subtractive hybridization provided herein are particularly suited for subtractive hybridization using amplified target RNAs.

Accordingly, the invention provides methods for performing subtractive hybridization, said methods comprising: (a) preparing multiple DNA copies of the complement of target polynucleotide from a first polynucleotide population using any of the amplification methods described herein; and (b) hybridizing the multiple copies to a second polynucleotide population, whereby a subpopulation of the second polynucleotide population forms a complex with DNA copies of the first polynucleotide population. The invention also provides methods for performing subtractive hybridization, said methods comprising: hybridizing multiple copies of the complement of at least one polynucleotide from a first polynucleotide population using any of the amplification methods described herein to a second polynucleotide population, whereby a subpopulation of the second population forms a complex with a copy from the copies of the first polynucleotide population. In preferred embodiments, the polynucleotide populations utilized in subtractive hybridization are RNA populations. In some embodiments, "driver" single stranded anti-sense DNA product of the methods of the invention is combined with tester (sense) RNA species. In some embodiments, "driver" single stranded antisense nucleic acid (generally, DNA) product is produced using the methods of the invention described herein.

In another aspect, the invention provides methods of differential amplification in which single stranded driver (antisense) DNA sequences that hybridize with tester RNA sequence are subjected to cleavage by an agent that cleaves RNA present in a DNA/RNA hybrid, such as RNase H. Cleavage of the RNA results in the inability to generate single stranded DNA product from the test RNA strands. Conversely, non-cleaved tester (i.e., tester RNA that did not hybridize to driver DNA molecules) may serve as a substrate for subsequent amplification. Amplified differentially expressed products have many uses, including as a differential expression probe, to produce differential expression libraries. Accordingly, the invention provides methods for differential amplification of one or more RNA template sequence, said method comprising: (a) preparing multiple polynucleotide (generally, DNA) copies of the complement of RNA from a first RNA population using any of the amplification methods described herein; (b) hybridizing the multiple copies to a second RNA population, whereby a subpopulation of the second RNA population forms a complex with a DNA copy; (c) cleaving RNA in the complex of step (b) with an enzyme that cleaves RNA from an RNA/DNA hybrid; and (d) amplifying an unhybridized subpopulation of the second RNA population, whereby multiple copies of single stranded DNA complementary to the unhybridized subpopulation of the second RNA population are generated. In some embodiments, step (d) is performed using any of the amplification methods described herein. In some embodiments, the methods comprise hybridizing multiple polynucleotide (generally, DNA) copies of the complement of at least one RNA sequences of interest from a first RNA population using any of the amplification methods described herein to a second RNA population, whereby a subpopulation of the second RNA population forms a complex with a DNA copy; (b) cleaving RNA in the complex of step (a) with an enzyme that cleaves RNA from an RNA/DNA hybrid; and (c) amplifying an unhybridized subpopulation of the second RNA population, whereby multiple copies of single stranded DNA complementary to the unhybridized subpopulation of the second RNA population are generated.

The following Examples are provided to illustrate, but not limit, the invention.

EXAMPLES

Example 1

Global Amplification of Human Genomic DNA Using a Composite Primer and Random Hexamer Primers Global amplification reactions were performed using composite primer IA20 and human genomic DNA as a template. The sequence of composite primer IA20 is as follows: IA20: 5'-GACGGAUGCGGUCUdCdCdAdGdTdGdT-3' (SEQ ID NO:1), where italics denote ribonucleotides, and "d" denotes deoxyribonucleotides.

Human genomic DNA (Clontech, Cat. No. 6550-1) was diluted in TE buffer and denatured by heating to 99° C. In some samples, DNA and primers were mixed in amplification buffer and heated at 96° C. for 2-4 minutes.

The following reaction mixture was used.
2 ng of pre-denatured human genomic DNA (approximately 600 copies)
2 µl of random hexamer N6 (final concentration 2.5 µM) (Qiagen-Operon; item No.: PolyN (6-mer));
0.5 µl (100 µM) composite primer IA20 (final concentration: 2.5 µM),
0.1 µl Bst DNA polymerase (0.04 U/µl) (New England BioLabs, Catalog No. M0275);
10 µl buffer (final concentration: 20 mM Tris-HCl, pH 8.5; 5 mM $MgCl_2$; RNasin, 0.3 U/µl; DTT, 0.5 mM; acetylated BSA, 0.1 µg/µl; T4 gp32 protein, 0.15 µg/µl)), and
RNase-free water to final volume of 15 µl.
The mixture was incubated at 30° C. for 5 minutes, followed by 5 minutes at 40° C., and 2 minutes at 50° C.

5 µl of enzyme mixture (RNase H, final concentration of 0.025 U/µl; and Bst DNA polymerase (large fragment), final concentration 0.2 U/µl) was added, and the reaction was incubated at 50° C. for 30-40 minutes. The reaction was stopped by incubation at 80° C. for 5 minutes to inactivate the enzymes.

Control reactions were prepared in which either composite primer, N6 random primers, or RNase H were omitted. In control reactions, the corresponding volume (of the omitted reagent) was replaced by water.

Figure 9:
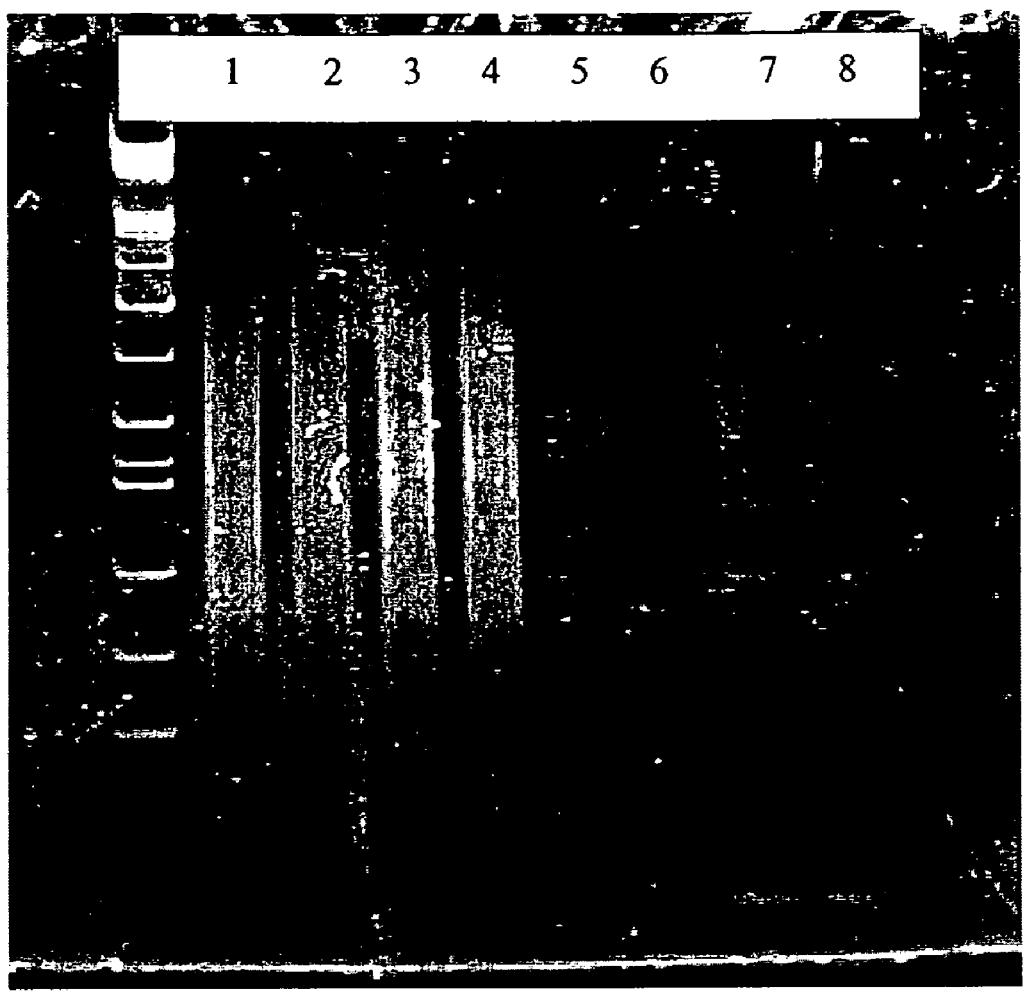
FIG. 9 shows a photograph of a gel showing amplified reaction product generated using a single randomly primed composite primer to amplify a multiplicity of template polynucleotide sequences from human genomic DNA.

Amplification reaction product was analyzed as follows. 0.5 µl of reaction mixture was loaded onto 4-20% gradient acrylamide gel and electrophoresed at 200-220 V constant voltage for 30 min. The gel was stained in 0.005 mg/ml Ethidium Bromide for 2 minutes and washed in water for 1 minute. The gel was then visualized and photographed on the AlphaImager 2200 system. The results are shown in FIG. 9. Lanes correspond to the reaction mixtures containing the following components:

Lanes #1-2: Complete reaction mixture
Lanes #3-4: Reaction lacking N6 random primer.
Lanes #5-6: Reaction lacking composite primer.
Lanes #7-8: Reaction lacking RNase H.

FIG. 9 shows that amplification product of varying molecular weight was produced in reactions containing the complete reaction mixture (described above), and in reaction lacking N6 random primers. However, reactions in which composite primer or RNase H were omitted did not show detectable reaction product.

Amplification product was quantified using the following procedure: reactions were prepared and processed as described above. Reaction mixture was diluted 100-fold and 2 µl of the diluted samples were used in Real Time PCR quantification with the following primer pairs that amplify a single copy sequence on Chromosome 7:

```
221PF2 (5'-AGTATCTGGCACATCTT-3' (SEQ ID NO:___))
``` and

```
221PR2 (5'-GGGAGATATTATTTGGC-3' (SEQ ID NO:___)).
```

Amplification with primers 221PF2 and 221 PR2 was expected to yield a 62 base pair PCR product. The PCR reaction mixture contained: 1 µl of 10 µM of each primer, 6 µl of water, 10 µl of 2×SYBR Green PCR Master Mix (Applied Biosystems), and 2 µl diluted reaction mixture (diluted as described above). A control reaction was conducted using 2 µl human genomic DNA, instead of amplification reaction product as a template.

The thermal cycling program used was: one cycle of 94° C. for 10 min., followed by 45 cycles of 94° C. for 30 sec., 55° C. for 30 sec., and 72° C. for 30 sec. The Real Time PCR quantification data were presented as Ct values (threshold cycle). The values obtained for quantification of amplification products were compared with that obtained for 2 µl human genomic DNA (labeled "non-amplified Genomic DNA" in Table 1). The dilution factor between the diluted global amplification products and the original human genomic DNA input into the amplification reactions is 1000 fold. The data were summarized in Table 1.

TABLE 1

Quantification of amplification products and target human genomic DNA employing Real Time PCR with SYBR Green. A single copy sequence on Chromosome 7 of human genomic DNA (221) was used for determination of amplification efficiency. Amplification efficiency is expressed as the relative amount of this single copy sequence in starting genomic DNA sample and following global amplification.

| Reaction components | Ct | Efficiency |
| --- | --- | --- |
| Complete | 29 | 4000 fold |
| No N6 random primers | 36 | 40 fold |
| No Composite primer | None | None |
| No RNase H | None | None |
| None (non amplified Genomic DNA) | 31 | None |

In a second experiment, human genomic DNA was amplified using composite primer IA20 essentially as described above. Following amplification, several target sequences were quantified using Real Time PCR essentially as described above. Chromosomal location of target sequences and PCR primer pairs are shown in Table 2. Table 2 shows the relative amount of target sequence following global amplification, and the amplification efficiency. Real Time PCR quantification data were presented as Ct values (threshold cycle).

TABLE 2

| Target location | Forward PCR primer | Reverse PCR primer | Real time Delta C(t) | Amplification fold |
|---|---|---|---|---|
| chromosome #6 | GGACGTGTGTTCCTGTTAA (SEQ ID NO_) | CACTTTGATCCTGAAAGACT (SEQ ID NO_) | 3.5 | 2000 |
| chromosome #7 | AGTATCTGGCACATCTT (SEQ ID NO:_) | GGGAGATATTATTTGGC (SEQ ID NO:_) | 4 | 3000 |
| chromosome #11 | AGGTTCCCAGCCTTGGTCC (SEQ ID NO_) | TGAGGCCATGTGTGTGGAAT (SEQ ID NO:_) | 2 | 800 |
| chromosome #12 | AATAATGTCCAGATATCTTGGT (SEQ ID NO:_) | TCCCTACTCCAGCTACTTCT (SEQ ID NO:_) | 2.5 | 1000 |
| chromosome #16 | CAGCAAGAACACAAGGGAC (SEQ ID NO_) | TCTTGAGAGCGAGGGCA (SEQ ID NO_) | 2.5 | 1000 |

In a third experiment, human genomic DNA was amplified using composite primer BSCA-128F essentially as described above. The sequence of composite primer BSCA-128F is:
5'-CGUAUUCUGACGACGUACUCdTd-CdAdGdCdCdT-3' (SEQ ID NO:2) where italics denote ribonucleotides, and "d" denotes deoxyribonucleotides.

Amplification reaction product was analyzed as described above. Amplification product of varying molecular weights was generated, suggesting that the composite primer permitted amplification from a multiplicity of template sequences.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention.

We claim:

1. A method for amplification of a template DNA, comprising:
   (a) incubating a reaction mixture, said reaction mixture comprising:
      (i) a template DNA:
      (ii) a first primer, wherein the first primer is hybridizable to a multiplicity of template sites, wherein the first primer is a population of different composite primers each comprising an RNA portion and a 3' DNA portion, wherein each composite primer comprises a 3' random sequence, and wherein each composite primer is a tailed primer that comprises a 5' portion that is not hybridizable to the template DNA tinder conditions in which the first primer hybridizes to the template DNA;
      (iii) a DNA-dependent DNA polymerase; and
      (iv) an RNA-dependent DNA polymerase;
      wherein the incubation is under conditions that permit generation of a complex comprising an RNA/DNA heteroduplex, wherein said complex comprising an RNA/DNA heteroduplex is produced by hybridization of the first primer to the template DNA, primer extension to generate a first primer extension product, hybridization of a second primer to the first primer extension product, and extension of the second primer to generate a second primer extension product; and
   (b) incubating a reaction mixture, said reaction mixture comprising
      (i) at least a portion of the reaction products generated according to step (a);
      (ii) an amplification primer, wherein said amplification primer is a composite primer comprising an RNA portion and a 3' DNA portion, wherein the amplification primer comprises some of the sequence of the first primer, and wherein the first primer and the amplification primer are different primers;
      (iii) a DNA-dependent DNA polymerase; and
      (iv) an agent that cleaves RNA from an RNA/DNA heteroduplex;
      wherein the incubation is under conditions that permit RNA cleavage, primer hybridization, primer extension, and displacement of the first primer extension product when its RNA is cleaved and another amplification primer binds to the second primer extension product and is extended, such that primer extension and strand displacement are repeated, whereby multiple copies of a an amplification product are generated.

2. The method of claim 1, wherein said DNA-dependent DNA polymerase and said RNA-dependent DNA polymerase of step (a) are the same enzyme.

3. The method of claim 1, wherein said DNA-dependent DNA polymerase and said RNA-dependent DNA polymerase of step (a) are different enzymes.

4. The method of claim 1, wherein said first primer and said second primer are the same primer.

5. The method of claim 1, wherein said first primer and said second primer are different primers.

6. The method of claim 1, wherein step (b) is initiated by the addition of an agent that cleaves RNA front an RNA/DNA heteroduplex to the reaction mixture of step (a).

7. The method of claim 1, wherein the agent that cleaves RNA from an RNA/DNA heteroduplex is an enzyme.

8. The method of claim 7, wherein said agent that cleaves RNA from an RNA/DNA heteroduplex is RNase H.

9. The method of claim 1, wherein the RNA portion of the first primer is 5' with respect to the 3' DNA portion.

10. The method of claim 9, wherein the RNA portion of the amplification primer is 5' with respect to the 3' DNA portion.

11. The method of claim 1, wherein the RNA portion of the amplification primer is 5' with respect to the 3' DNA portion.

12. The method of claim 11, wherein the 5' RNA portion of the amplification primer is adjacent to the 3' DNA portion.

13. The method of claim 1, wherein the RNA portion of the first primer consists of about 7 to about 50 nucleotides.

14. The method of claim 13, wherein the DNA portion of the first primer consists of about 5 to about 20 nucleotides.

15. The method of claim 1, wherein the RNA portion of the amplification primer consists of about 7 to about 50 nucleotides.

16. The method of claim 15, wherein the DNA portion of the amplification primer consists of about 5 to about 20 nucleotides.

17. The method of claim 1, wherein the reaction mixture of step (b) further comprises a non-canonical nucleotide.

18. The method of claim 17, wherein the non-canonical nucleotide is dUTP.

19. The method of claim 1, wherein the reaction mixture of step (b) further comprises a labeled nucleotide.

20. A method for amplification of a template DNA, comprising:
 incubating a reaction mixture, said reaction mixture comprising:
  (a) a complex comprising a RNA/DNA partial heteroduplex, wherein the complex is generated by incubating a first reaction mixture, said first reaction mixture comprising:
   (i) a template DNA;
   (ii) a first primer; wherein the first primer is hybridizable to a multiplicity of template sites, wherein the first primer is a population of different composite primers each comprising an RNA portion and a 3' DNA portion, wherein the composite primer comprises a 3' random sequence, and wherein the composite primer is a tailed primer that comprises a 5' portion that is not hybridizable to the template DNA under conditions in which the first primer hybridizes to the template DNA;
   (iii) a DNA-dependent DNA polymerase; and
   (iv) an RNA-dependent DNA polymerase;
  wherein the incubation is under conditions that permit hybridization of the first primer to the template DNA, primer extension to generate a first primer extension product, hybridization of a second primer to the first primer extension product, and extension of the second primer to generate a second primer extension product, whereby a complex comprising an RNA/DNA partial heteroduplex is generated;
  (b) an amplification primer, wherein the amplification primer is a composite primer comprising an RNA portion and a 3' DNA portion, wherein the amplification primer comprises some of the sequence of the first primer, and wherein the first primer and the amplification primer are different primers;
  (c) a DNA-dependent DNA polymerase; and
  (d) an agent that cleaves RNA from an RNA/DNA heteroduplex;
  wherein the incubation is under conditions that permit RNA cleavage, primer hybridization, primer extension, and displacement of the first primer extension product when its RNA is cleaved and another amplification primer binds to the second primer extension product and is extended, such that primer extension and strand displacement are repeated, whereby multiple copies of an amplification product are generated.

21. The method of claim 20, wherein the agent that cleaves RNA from an RNA/DNA heteroduplex is an enzyme.

22. The method of claim 21, wherein the enzyme that cleaves RNA from an RNA/DNA heteroduplex is RNase H.

23. The method of claim 21, wherein said DNA-dependent DNA polymerase and said enzyme that cleaves RNA from an RNA/DNA heteroduplex are the same enzyme.

24. The method of claim 23, wherein said DNA-dependent DNA polymerase and said enzyme that cleaves RNA from an RNA/DNA heteroduplex are different enzymes.

25. The method of claim 20, wherein the RNA portion of the amplification primer is 5' with respect to the 3'-DNA portion.

26. The method of claim 25, wherein the 5' RNA portion of the amplification primer is adjacent to the 3' DNA portion.

27. The method of claim 20, wherein the RNA portion of the amplification primer consists of about 7 to about 50 nucleotides.

28. The method of claim 27, wherein the DNA portion of the amplification primer consists of about 5 to about 20 nucleotides.

29. The method of claim 20, wherein the RNA portion of the amplification primer consists of about 10 to about 50 nucleotides.

30. The method of claim 29, wherein the DNA portion of the amplification primer consists of about 7 to about 20 nucleotides.

31. The method of claim 20, wherein the reaction mixture further comprises a non-canonical nucleotide.

32. The method of claim 31, wherein the non-canonical nucleotide is dUTP.

33. The method of claim 20, wherein the reaction mixture further comprises a labeled nucleotide.

34. A method for amplification of a template DNA, comprising:
 incubating a reaction mixture, said reaction mixture comprising:
  (a) a complex of a first primer extension product and a second primer extension product, wherein the first primer extension product is generated by extension of a first primer hybridized to the template DNA with a DNA polymerase, wherein the first primer is a hybridizable to a multiplicity of template polynucleotide sites, wherein the first primer is a population of different composite primers each comprising an RNA portion and a 3' DNA portion, wherein each composite primer comprises a 3' random sequence, and wherein each composite primer is a tailed primer that comprises a 5' portion that is not hybridizable to the template DNA under conditions in which the first primer hybridizes to the template DNA, and wherein the second primer extension product is generated by extension of a second primer hybridized to the first primer extension product;
  (b) an amplification primer, wherein the amplification is a composite primer comprising an RNA portion and a 3' DNA portion, wherein the amplification primer comprises some of the sequence of the first primer, wherein the first primer and the amplification primer are different primers, and wherein the amplification primer is hybridizable to the second primer extension product;

(c) a DNA-dependent DNA polymerase; and (d) an agent that cleaves RNA from an RNA/DNA heteroduplex;

wherein the incubation is under conditions that permit RNA cleavage, primer hybridization, primer extension, and displacement of the first primer extension product from the second primer extension product when its RNA is cleaved and another amplification primer binds and is extended, such that primer extension and strand displacement are repeated, whereby multiple copies of an amplification product are generated.

35. The method of claim 34, wherein said agent that cleaves RNA from a RNA/DNA heteroduplex is an enzyme.

36. The method of claim 35, wherein the enzyme that cleaves RNA from a RNA/DNA heteroduplex is RNase H.

37. The method of claim 35, wherein said DNA-dependent DNA polymerase and the enzyme that cleaves RNA from an RNA/DNA heteroduplex are the same enzyme.

38. The method of claim 35, wherein said DNA-dependent DNA polymerase and the enzyme that cleaves RNA from an RNA/DNA heteroduplex are different enzymes.

39. The method of claim 34, wherein the RNA portion of the amplification primer is 5' with respect to the 3' DNA portion.

40. The method of claim 39, wherein the 5' RNA portion of the amplification primer is adjacent to the 3' DNA portion.

41. The method of claim 34, wherein the RNA portion of the amplification primer consists of about 7 to about 50 nucleotides.

42. The method of claim 41, wherein the DNA portion of the amplification primer consists of about 5 to about 20 nucleotides.

43. The method of claim 34, wherein the RNA portion of the amplification primer consists of about 10 to about 50 nucleotides.

44. The method of claim 43, wherein the DNA portion of the amplification primer consists of about 7 to about 20 nucleotides.

45. The method of claim 34, wherein the reaction mixture further comprises a non-canonical nucleotide.

46. The method of claim 45, wherein the non-canonical nucleotide is dUTP.

47. The method of claim 34, wherein the reaction mixture further comprises a labeled nucleotide.

48. A method for amplification of a template DNA, comprising:

(a) randomly priming a template DNA with a first primer, wherein said first primer is hybridizable to a multiplicity of template polynucleotide sites, wherein the first primer is a population of different composite primers each comprising an RNA portion and a 3' DNA portion, and wherein each composite primer is a tailed primer that comprises a 5' portion that is not hybridizable to the template DNA under conditions in which the first primer hybridizes to the template DNA;

(b) extending said first primer with a DNA polymerase to generate a first primer extension product;

(c) hybridizing a second primer to the first primer extension product;

(d) extending said second primer with a DNA-dependent DNA polymerase and an RNA-dependent polymerase to generate a second primer extension product, whereby a complex comprising an RNA/DNA heteroduplex is generated;

(e) cleaving RNA from the first primer with an agent that cleaves RNA from a RNA/DNA heteroduplex;

(f) hybridizing an amplification primer to the second primer extension product, wherein said amplification primer is a composite primer comprising a RNA portion and a 3' DNA portion, wherein the amplification primer comprises some of the sequence of the first primer, and wherein the first primer and the amplification primer are different primers;

(g) extending the hybridized amplification primer by strand displacement DNA synthesis;

(h) cleaving RNA from the amplification primer with an agent that cleaves RNA from a RNA/DNA heteroduplex, such that another amplification primer hybridizes and is extended, whereby multiple copies of an amplification product are generated.

49. The method of claim 48, wherein the agent that cleaves RNA from an RNA/DNA heteroduplex is an enzyme.

50. The method of claim 49, wherein the enzyme that cleaves RNA from an RNA/DNA heteroduplex is RNase H.

51. The method of claim 48, wherein the DNA polymerase of step (b) is a DNA-dependent DNA polymerase.

52. The method of claim 48, wherein the DNA-dependent DNA polymerase and the RNA-dependent DNA polymerase are the same enzyme.

53. The method of claim 48, wherein the DNA-dependent DNA polymerase and the RNA-dependent DNA polymerase are different enzymes.

54. The method of claim 48, wherein the RNA portion of the first primer is 5' with respect to the 3' DNA portion.

55. The method of claim 48, wherein the RNA portion of the amplification primer is 5' with respect to the 3' DNA portion.

56. The method of claim 55, wherein the 5' RNA portion of the amplification primer is adjacent to the 3' DNA portion.

57. The method of claim 54, wherein the 5' RNA portion of the first primer is adjacent to the 3' DNA portion.

58. The method of claim 48, wherein the RNA portion of the first primer consists of about 7 to about 50 nucleotides.

59. The method of claim 58, wherein the DNA portion of the first primer consists of about 5 to about 20 nucleotides.

60. The method of claim 48, wherein the RNA portion of the amplification primer consists of about 7 to about 50 nucleotides.

61. The method of claim 60, wherein the DNA portion of the amplification primer consists of about 5 to about 20 nucleotides.

62. The method of claim 48, wherein step (g) is carried out in the presence of a non-canonical nucleotide.

63. The method of claim 62, wherein the non-canonical nucleotide is dUTP.

64. The method of claim 48, wherein step (g) is carried out in the presence of a labeled nucleotide.

65. The method of claim 20, wherein the RNA portion of the first primer is 5' with respect to the 3'-DNA portion.

66. The method of claim 65, wherein the 5' RNA portion of the first primer is adjacent to the 3' DNA portion.

67. The method of claim 20, wherein said first primer and said second primer are the same primer.

68. The method of claim 67, wherein said first primer and said second primer are different primers.

69. The method of claim 34, wherein the RNA portion of the first primer is 5' with respect to the 3'-DNA portion.

70. The method of claim 69, wherein the 5' RNA portion of the first primer is adjacent to the 3' DNA portion.

71. The method of claim 34, wherein said first primer and said second primer are the same primer.

72. The method of claim 71, wherein said first primer and said second primer are different primers.

73. The method of any of claims 1, 20, 34, or 48, wherein said template DNA is genomic DNA.

74. The method of claim 73, wherein said genomic DNA comprises a multiplicity of genomic DNA templates.

* * * * *

UNITED STATES PATENT AND TRADEMARK OFFICE
CERTIFICATE OF CORRECTION

PATENT NO. : 7,402,386 B2  Page 1 of 1
APPLICATION NO. : 10/824829
DATED : July 22, 2008
INVENTOR(S) : Nurith Kurn et al.

It is certified that error appears in the above-identified patent and that said Letters Patent is hereby corrected as shown below:

Title page, item [73]

Please change "Nugen Technologies, Inc." with --NuGEN Technologies, Inc.--

In Column 55, line 51 (Claim 1), please replace "tinder" with --under--.

In Column 56, line 56 (Claim 1), please delete the "a" preceeding "an amplification".

Signed and Sealed this

Twenty-first Day of October, 2008

JON W. DUDAS
*Director of the United States Patent and Trademark Office*

UNITED STATES PATENT AND TRADEMARK OFFICE
CERTIFICATE OF CORRECTION

PATENT NO.         : 7,402,386 B2                                    Page 1 of 1
APPLICATION NO.    : 10/824829
DATED              : July 22, 2008
INVENTOR(S)        : Kurn et al.

It is certified that error appears in the above-identified patent and that said Letters Patent is hereby corrected as shown below:

On the cover page,

Item [*] Notice:      Subject to any disclaimer, the term of this patent is extended or adjusted under 35 USC 154(b) by (41) days Delete the phrase "by 41 days" and insert -- by 140 days --

Signed and Sealed this

Twenty-third Day of December, 2008

JON W. DUDAS
*Director of the United States Patent and Trademark Office*

SEQUENCE LISTING

<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(14)
<223> OTHER INFORMATION: Ribonucleotides
<220> FEATURE:
<221> NAME/KEY: misc_feature
<222> LOCATION: (15)...(21)
<223> OTHER INFORMATION: Deoxyribonucleotides

<400> SEQUENCE: 1
gacggaugcg gucudcdcda dgdtdgdt                                      28

<210> SEQ ID NO 2
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(21)
<223> OTHER INFORMATION: Ribonucleotides
<220> FEATURE:
<221> NAME/KEY: misc_feature
<222> LOCATION: (22)...(34)
<223> OTHER INFORMATION: Deoxyribonucleotides

<400> SEQUENCE: 2
cguauucuga cgacguacuc dtdcdadgdc dcdt                               34

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
agtatctggc acatctt                                                17

<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4
gggagatatt atttggc                                                17

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ggacgtgtgt tcctgttaa                                              19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cactttgatc ctgaaagact                                             20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
aggttcccag ccttggtcc                                              19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgaggccatg tgtgtggaat                                             20

<210> SEQ ID NO 9
<211> LENGTH: 22
<212> TYPE: DNA
<213> ORGANISM: Artificial Sequence
<220> FEATURE:
<223> OTHER INFORMATION: Primer -continued

```
<400> SEQUENCE: 9
aataatgtcc agatatcttg gt                                                22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tccctactcc agctacttct                                                   20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cagcaagaac acaagggac                                                    19

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
tcttgagagc gagggca                                                      17
```